(12) United States Patent
Hanson et al.

(10) Patent No.: US 9,386,996 B2
(45) Date of Patent: *Jul. 12, 2016

(54) NAVIGATION AND POSITIONING INSTRUMENTS FOR JOINT REPAIR

(71) Applicant: ZIMMER KNEE CREATIONS, INC., Exton, PA (US)

(72) Inventors: Shaun B. Hanson, West Chester, PA (US); Christopher D. Mandeen, West Chester, PA (US); David L. Nichols, West Chester, PA (US); Thomas A. Russell, Eads, TN (US)

(73) Assignee: ZIMMER KNEE CREATIONS, INC., Exton, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/695,516

(22) Filed: Apr. 24, 2015

(65) Prior Publication Data

US 2015/0230807 A1 Aug. 20, 2015

Related U.S. Application Data

(63) Continuation of application No. 14/143,883, filed on Dec. 30, 2013, now Pat. No. 9,033,987, which is a continuation of application No. 12/950,061, filed on Nov. 19, 2010, now Pat. No. 8,617,166.

(60) Provisional application No. 61/377,313, filed on Aug. 26, 2010, provisional application No. 61/263,170, filed on Nov. 20, 2009.

(51) Int. Cl.
*A61B 17/17* (2006.01)
*A61B 19/00* (2006.01)

(52) U.S. Cl.
CPC .............. *A61B 17/17* (2013.01); *A61B 19/54* (2013.01); *A61B 2019/5437* (2013.01)

(58) Field of Classification Search
CPC ....................................................... A61B 17/17
See application file for complete search history.

(56) References Cited

U.S. PATENT DOCUMENTS

| 2,697,433 A | 12/1954 | Zehnder |
| 3,913,187 A | 10/1975 | Okuida |

(Continued)

FOREIGN PATENT DOCUMENTS

| CN | 101048111 A | 10/2007 |
| CN | 101102724 A | 1/2008 |

(Continued)

OTHER PUBLICATIONS

"U.S. Appl. No. 12/950,230, Final Office Action mailed Jan. 13, 2015", 10 pgs.

(Continued)

*Primary Examiner* — Andrew Yang
(74) *Attorney, Agent, or Firm* — Schwegman Lundberg & Woessner, P.A.

(57) ABSTRACT

An instrument for controlled delivery of a device to a target area near a defect of a bone is provided. The instrument comprises a guide frame having a plurality of device portals, each portal defining a trajectory. The guide frame further includes visual markers for aligning the guide frame to an anatomical landmark on the bone to be treated. The instrument also includes a holder for releasable attachment with the guide frame. Each device portal is configured to provide accurate and controlled delivery of the device to the target area. In one example, the markers are radiopaque, and are visualized through fluoroscopy. A method of using the instrument is also provided.

19 Claims, 14 Drawing Sheets

(56) References Cited

U.S. PATENT DOCUMENTS

| | | | |
|---|---|---|---|
| 3,988,783 | A | 11/1976 | Treace |
| 4,037,592 | A * | 7/1977 | Kronner ............ A61B 17/1703 606/97 |
| 4,108,165 | A | 8/1978 | Kopp et al. |
| 4,360,012 | A | 11/1982 | Mcharrie et al. |
| 4,653,487 | A | 3/1987 | Maale |
| 4,781,182 | A | 11/1988 | Purnell et al. |
| 4,815,454 | A | 3/1989 | Dozier, Jr. |
| 4,834,757 | A | 5/1989 | Brantigan |
| 4,883,048 | A | 11/1989 | Purnell et al. |
| 4,911,153 | A | 3/1990 | Border |
| 4,920,958 | A | 5/1990 | Walt et al. |
| 4,964,861 | A | 10/1990 | Agee et al. |
| 5,098,383 | A | 3/1992 | Hemmy et al. |
| 5,163,940 | A | 11/1992 | Bourque |
| 5,178,164 | A | 1/1993 | Allen |
| 5,247,934 | A | 9/1993 | Wehrli et al. |
| 5,298,254 | A | 3/1994 | Prewett et al. |
| 5,324,295 | A | 6/1994 | Shapiro |
| 5,342,363 | A | 8/1994 | Richelsoph |
| 5,370,646 | A | 12/1994 | Reese et al. |
| 5,439,684 | A | 8/1995 | Prewett et al. |
| 5,458,602 | A | 10/1995 | Goble et al. |
| 5,514,137 | A | 5/1996 | Coutts |
| 5,556,429 | A | 9/1996 | Felt |
| 5,595,193 | A | 1/1997 | Walus et al. |
| 5,609,636 | A | 3/1997 | Kohrs et al. |
| 5,618,549 | A | 4/1997 | Patat et al. |
| 5,681,320 | A | 10/1997 | McGuire |
| 5,741,266 | A | 4/1998 | Moran et al. |
| 5,743,916 | A | 4/1998 | Greenberg et al. |
| 5,755,809 | A | 5/1998 | Cohen et al. |
| 5,766,221 | A | 6/1998 | Benderev et al. |
| 5,827,289 | A | 10/1998 | Reiley et al. |
| 5,868,749 | A | 2/1999 | Reed |
| 5,888,220 | A | 3/1999 | Felt et al. |
| 5,891,150 | A | 4/1999 | Chan |
| 5,928,239 | A | 7/1999 | Mirza |
| 5,968,047 | A | 10/1999 | Reed |
| 5,968,050 | A | 10/1999 | Torrie |
| 5,972,015 | A | 10/1999 | Scribner et al. |
| 6,010,502 | A | 1/2000 | Bagby |
| 6,036,696 | A | 3/2000 | Lambrecht et al. |
| 6,039,742 | A | 3/2000 | Krettek et al. |
| 6,048,346 | A | 4/2000 | Reiley et al. |
| 6,066,154 | A | 5/2000 | Reiley et al. |
| 6,110,211 | A | 8/2000 | Weiss |
| 6,111,164 | A | 8/2000 | Rainey et al. |
| 6,120,511 | A | 9/2000 | Chan |
| 6,140,452 | A | 10/2000 | Felt et al. |
| 6,143,030 | A | 11/2000 | Schroder |
| 6,162,225 | A | 12/2000 | Gertzman et al. |
| 6,214,013 | B1 | 4/2001 | Lambrecht et al. |
| 6,235,043 | B1 | 5/2001 | Reiley et al. |
| 6,241,734 | B1 | 6/2001 | Scribner et al. |
| 6,248,110 | B1 | 6/2001 | Reiley et al. |
| 6,248,131 | B1 | 6/2001 | Felt et al. |
| 6,254,605 | B1 | 7/2001 | Howell |
| 6,267,770 | B1 | 7/2001 | Truwit |
| 6,270,528 | B1 | 8/2001 | McKay |
| 6,283,942 | B1 | 9/2001 | Staehlin et al. |
| 6,285,901 | B1 | 9/2001 | Taicher et al. |
| 6,287,313 | B1 | 9/2001 | Sasso |
| 6,294,187 | B1 | 9/2001 | Boyce et al. |
| 6,306,177 | B1 | 10/2001 | Felt et al. |
| 6,342,056 | B1 | 1/2002 | Mac-Thiong et al. |
| 6,358,251 | B1 | 3/2002 | Mirza |
| 6,368,322 | B1 | 4/2002 | Luks et al. |
| 6,395,007 | B1 | 5/2002 | Bhatnagar et al. |
| 6,398,811 | B1 | 6/2002 | Mckay |
| 6,423,083 | B2 | 7/2002 | Reiley et al. |
| 6,486,232 | B1 | 11/2002 | Wise et al. |
| 6,506,192 | B1 | 1/2003 | Gertzman et al. |
| 6,506,785 | B2 | 1/2003 | Evans et al. |
| 6,520,969 | B2 | 2/2003 | Lambrecht et al. |
| 6,527,773 | B1 | 3/2003 | Lin et al. |
| 6,533,794 | B2 | 3/2003 | Chakeres |
| 6,564,083 | B2 | 5/2003 | Stevens |
| 6,607,561 | B2 | 8/2003 | Brannon |
| 6,613,054 | B2 | 9/2003 | Scribner et al. |
| 6,645,213 | B2 | 11/2003 | Sand et al. |
| 6,663,647 | B2 | 12/2003 | Reiley et al. |
| 6,719,761 | B1 | 4/2004 | Reiley et al. |
| 6,726,691 | B2 | 4/2004 | Osorio et al. |
| 6,730,124 | B2 | 5/2004 | Steiner |
| 6,746,451 | B2 | 6/2004 | Middleton et al. |
| 6,767,369 | B2 | 7/2004 | Boyer, II et al. |
| 6,814,736 | B2 | 11/2004 | Reiley et al. |
| 6,827,720 | B2 | 12/2004 | Leali |
| 6,863,672 | B2 | 3/2005 | Reiley et al. |
| 6,863,899 | B2 | 3/2005 | Koblish et al. |
| 6,869,434 | B2 | 3/2005 | Choi |
| 6,875,212 | B2 | 4/2005 | Shaolian et al. |
| 6,887,246 | B2 | 5/2005 | Bhatnagar et al. |
| 6,899,719 | B2 | 5/2005 | Reiley et al. |
| 6,917,827 | B2 | 7/2005 | Kienzle, III |
| 6,918,916 | B2 | 7/2005 | Gobel et al. |
| 6,923,813 | B2 | 8/2005 | Phillips |
| 6,979,341 | B2 | 12/2005 | Scribner et al. |
| 6,981,981 | B2 | 1/2006 | Reiley |
| 7,001,431 | B2 | 2/2006 | Bao et al. |
| 7,029,477 | B2 | 4/2006 | Grimm |
| 7,063,701 | B2 | 6/2006 | Michelson |
| 7,063,702 | B2 | 6/2006 | Michelson |
| 7,087,082 | B2 | 8/2006 | Paul et al. |
| 7,094,239 | B1 | 8/2006 | Michelson |
| 7,115,146 | B2 | 10/2006 | Boyer, II et al. |
| 7,144,414 | B2 | 12/2006 | Harvie et al. |
| 7,153,305 | B2 | 12/2006 | Johnson et al. |
| 7,153,306 | B2 | 12/2006 | Ralph et al. |
| 7,153,307 | B2 | 12/2006 | Scribner et al. |
| 7,155,306 | B2 | 12/2006 | Haitin et al. |
| 7,160,305 | B2 | 1/2007 | Schmieding |
| 7,192,431 | B2 | 3/2007 | Hangody et al. |
| 7,226,481 | B2 | 6/2007 | Kuslich |
| 7,241,303 | B2 | 7/2007 | Reiss et al. |
| 7,250,055 | B1 | 7/2007 | Vanderwalle |
| 7,252,671 | B2 | 8/2007 | Scribner |
| 7,261,716 | B2 | 8/2007 | Strobel et al. |
| 7,261,720 | B2 | 8/2007 | Stevens et al. |
| 7,313,430 | B2 | 12/2007 | Urquhart et al. |
| 7,399,306 | B2 | 7/2008 | Reiley et al. |
| 7,410,947 | B2 | 8/2008 | Rueger et al. |
| 7,448,264 | B2 | 11/2008 | Boyce et al. |
| 7,458,977 | B2 | 12/2008 | McGinley et al. |
| 7,468,075 | B2 | 12/2008 | Lang et al. |
| 7,476,226 | B2 | 1/2009 | Weikel et al. |
| 7,477,770 | B2 | 1/2009 | Wehrli et al. |
| 7,485,119 | B2 | 2/2009 | Thelen et al. |
| 7,488,348 | B2 | 2/2009 | Truncale et al. |
| 7,491,205 | B1 | 2/2009 | Michelson |
| 7,507,240 | B2 | 3/2009 | Olsen |
| 7,534,226 | B2 | 5/2009 | Mernoe et al. |
| 7,545,964 | B2 | 6/2009 | Lang et al. |
| 7,550,007 | B2 | 6/2009 | Malinin |
| 7,550,011 | B2 | 6/2009 | Mckay et al. |
| 7,556,295 | B2 | 7/2009 | Holzheu |
| 7,559,932 | B2 | 7/2009 | Truckai et al. |
| 7,575,578 | B2 | 8/2009 | Wetzler et al. |
| 7,594,917 | B2 | 9/2009 | Whittaker et al. |
| 7,608,097 | B2 | 10/2009 | Kyle |
| 7,608,098 | B1 | 10/2009 | Stone |
| 7,643,664 | B2 | 1/2010 | Wehrli et al. |
| 7,682,378 | B2 | 3/2010 | Truckai et al. |
| 7,704,256 | B2 | 4/2010 | Sand et al. |
| 7,708,742 | B2 | 5/2010 | Scribner et al. |
| 7,713,273 | B2 | 5/2010 | Krueer et al. |
| 7,731,720 | B2 | 6/2010 | Sand et al. |
| 7,753,963 | B2 | 7/2010 | Boyer, II et al. |
| 7,769,213 | B2 | 8/2010 | Gregory et al. |
| 7,771,431 | B2 | 8/2010 | Scribner et al. |
| 7,789,912 | B2 | 9/2010 | Manzi et al. |
| 7,811,290 | B2 | 10/2010 | Rabiner |
| 7,837,733 | B2 | 11/2010 | Collins et al. |

(56) References Cited

U.S. PATENT DOCUMENTS

| | | |
|---|---|---|
| 7,837,740 B2 | 11/2010 | Semler et al. |
| 7,840,247 B2 | 11/2010 | Liew et al. |
| 7,846,206 B2 | 12/2010 | Oglaza et al. |
| 7,879,038 B2 | 2/2011 | Reiley et al. |
| 7,879,099 B2 | 2/2011 | Zipnick |
| 7,887,543 B2 | 2/2011 | Sand et al. |
| 7,887,546 B2 | 2/2011 | Gil |
| 7,896,885 B2 | 3/2011 | Miniaci et al. |
| 7,901,408 B2 | 3/2011 | Ek |
| 7,901,457 B2 | 3/2011 | Truncale et al. |
| 7,905,924 B2 | 3/2011 | White |
| 7,914,539 B2 | 3/2011 | Stone et al. |
| 7,927,339 B2 | 4/2011 | Ralph et al. |
| 7,931,840 B2 | 4/2011 | Michelson |
| 7,938,835 B2 | 5/2011 | Boucher et al. |
| 7,959,638 B2 | 6/2011 | Osorio et al. |
| 7,985,231 B2 | 7/2011 | Sankaran |
| 8,029,511 B2 | 10/2011 | Bowman et al. |
| 8,062,364 B1 | 11/2011 | Sharkey et al. |
| 8,070,753 B2 | 12/2011 | Truckai et al. |
| 8,092,480 B2 | 1/2012 | Layne et al. |
| 8,133,226 B2 | 3/2012 | Chou et al. |
| 8,142,462 B2 | 3/2012 | Middleton |
| 8,152,813 B2 | 4/2012 | Osorio et al. |
| 8,168,692 B2 | 5/2012 | Wenz |
| 8,187,327 B2 | 5/2012 | Edidin et al. |
| 8,246,681 B2 | 8/2012 | Osorio et al. |
| 8,608,802 B2 | 12/2013 | Bagga et al. |
| 8,617,166 B2 | 12/2013 | Hanson et al. |
| 8,617,176 B2 | 12/2013 | Lizardi et al. |
| 8,636,745 B2 | 1/2014 | Almutairi et al. |
| 8,801,800 B2 | 8/2014 | Bagga et al. |
| 8,821,504 B2 | 9/2014 | Sharkey et al. |
| 8,864,768 B2 | 10/2014 | Hanson et al. |
| 8,906,032 B2 | 12/2014 | Hanson et al. |
| 8,951,261 B2 | 2/2015 | Sharkey et al. |
| 9,033,987 B2 | 5/2015 | Hanson et al. |
| 9,119,721 B2 | 9/2015 | Sharkey et al. |
| 9,259,257 B2 | 2/2016 | Bagga et al. |
| 9,271,835 B2 | 3/2016 | Bagga |
| 2002/0029084 A1 | 3/2002 | Paul et al. |
| 2002/0151897 A1 | 10/2002 | Zirkie, Jr. |
| 2003/0009235 A1 | 1/2003 | Manrique et al. |
| 2003/0097135 A1 | 5/2003 | Penenberg |
| 2003/0105468 A1 | 6/2003 | Gorek |
| 2003/0138473 A1 | 7/2003 | Koblish et al. |
| 2003/0220651 A1 | 11/2003 | Pusnik et al. |
| 2003/0225456 A1 | 12/2003 | Ek |
| 2004/0002759 A1 | 1/2004 | Ferree |
| 2004/0010261 A1 | 1/2004 | Hoag et al. |
| 2004/0106925 A1 | 6/2004 | Culbert |
| 2004/0127987 A1 | 7/2004 | Evans et al. |
| 2004/0167538 A1 | 8/2004 | Gerber et al. |
| 2005/0075641 A1 | 4/2005 | Singhatat et al. |
| 2005/0119219 A1 | 6/2005 | Bellini et al. |
| 2005/0119753 A1 | 6/2005 | Mcgahan et al. |
| 2005/0149022 A1 | 7/2005 | Shaolian et al. |
| 2005/0159812 A1 | 7/2005 | Dinger, III et al. |
| 2005/0177171 A1 | 8/2005 | Wetzler et al. |
| 2005/0182418 A1 | 8/2005 | Boyd et al. |
| 2005/0203622 A1 | 9/2005 | Steiner et al. |
| 2005/0203623 A1 | 9/2005 | Steiner et al. |
| 2005/0256527 A1 | 11/2005 | Delfosse et al. |
| 2005/0267584 A1 | 12/2005 | Burdulis, Jr. et al. |
| 2005/0288795 A1 | 12/2005 | Bagga et al. |
| 2006/0052791 A1 | 3/2006 | Hagen et al. |
| 2006/0064164 A1 | 3/2006 | Thelen et al. |
| 2006/0084986 A1 | 4/2006 | Grinberg et al. |
| 2006/0247642 A1 | 11/2006 | Stone et al. |
| 2006/0271059 A1 | 11/2006 | Reay-Young et al. |
| 2007/0055280 A1 | 3/2007 | Osorio et al. |
| 2007/0100462 A1 | 5/2007 | Lang et al. |
| 2007/0127987 A1 | 6/2007 | Altenbuchner |
| 2007/0225813 A1 | 9/2007 | Haines |
| 2007/0276370 A1 | 11/2007 | Altarac et al. |
| 2007/0282346 A1 | 12/2007 | Scribner et al. |
| 2008/0027434 A1 | 1/2008 | Zucherman et al. |
| 2008/0039857 A1 | 2/2008 | Giersch et al. |
| 2008/0039866 A1 | 2/2008 | Stetz et al. |
| 2008/0077251 A1 | 3/2008 | Chen et al. |
| 2008/0103506 A1 | 5/2008 | Volpi et al. |
| 2008/0195115 A1 | 8/2008 | Oren et al. |
| 2008/0243127 A1 | 10/2008 | Lang et al. |
| 2008/0281331 A1 | 11/2008 | Fritzinger et al. |
| 2008/0288006 A1 | 11/2008 | Brannon |
| 2008/0306490 A1 | 12/2008 | Lakin et al. |
| 2009/0062797 A1 | 3/2009 | Huebner et al. |
| 2009/0069901 A1 | 3/2009 | Truncale et al. |
| 2009/0093813 A1 | 4/2009 | Elghazaly |
| 2009/0204158 A1 | 8/2009 | Sweeney |
| 2010/0015202 A1 | 1/2010 | Semler et al. |
| 2010/0076503 A1 | 3/2010 | Beyar et al. |
| 2010/0145451 A1 | 6/2010 | Dee |
| 2010/0160970 A1 | 6/2010 | Sevrain |
| 2010/0179549 A1 | 7/2010 | Keller et al. |
| 2010/0274254 A1 | 10/2010 | Boileau et al. |
| 2011/0125156 A1 | 5/2011 | Sharkey et al. |
| 2011/0125157 A1 | 5/2011 | Sharkey et al. |
| 2011/0125159 A1 | 5/2011 | Hanson et al. |
| 2011/0125160 A1 | 5/2011 | Bagga et al. |
| 2011/0125200 A1 | 5/2011 | Hanson et al. |
| 2011/0125201 A1 | 5/2011 | Hanson et al. |
| 2011/0125264 A1 | 5/2011 | Bagga et al. |
| 2011/0125265 A1 | 5/2011 | Bagga et al. |
| 2011/0125272 A1 | 5/2011 | Bagga et al. |
| 2014/0074103 A1 | 3/2014 | Mandeen et al. |
| 2014/0107781 A1 | 4/2014 | Bagga et al. |
| 2014/0114369 A1 | 4/2014 | Hanson et al. |
| 2014/0350683 A1 | 11/2014 | Sharkey et al. |
| 2014/0350685 A1 | 11/2014 | Bagga et al. |
| 2015/0025589 A1 | 1/2015 | Hanson et al. |
| 2015/0257886 A1 | 9/2015 | Sharkey et al. |

FOREIGN PATENT DOCUMENTS

| | | |
|---|---|---|
| CN | 101460105 A | 6/2009 |
| CN | 102770067 A | 11/2012 |
| CN | 102781348 A | 11/2012 |
| CN | 102740784 B | 9/2015 |
| EP | 2501303 A1 | 9/2012 |
| EP | 2501306 A1 | 9/2012 |
| EP | 2501314 A1 | 9/2012 |
| EP | 2501342 A1 | 9/2012 |
| WO | WO-03084412 A1 | 10/2003 |
| WO | WO-2005079881 A1 | 9/2005 |
| WO | WO-2008155772 A1 | 12/2008 |
| WO | WO-2011063240 A1 | 5/2011 |
| WO | WO-2011063250 A1 | 5/2011 |
| WO | WO-2011063257 A1 | 5/2011 |
| WO | WO-2011063267 A1 | 5/2011 |
| WO | WO-2011063279 A1 | 5/2011 |
| WO | WO-2011063281 A1 | 5/2011 |

OTHER PUBLICATIONS

"U.S. Appl. No. 12/950,230, Non Final Office Action mailed Apr. 15, 2015", 10 pgs.

"U.S. Appl. No. 12/950,230, Response filed Mar. 24, 2015 to Final Office Action mailed Jan. 13, 2015", 11 pgs.

"U.S. Appl. No. 12/950,273, Advisory Action mailed May 12, 2015", 3 pgs.

"U.S. Appl. No. 12/950,273, Final Office Action mailed Feb. 4, 2015", 28 pgs.

"U.S. Appl. No. 12/950,273, Response filed May 4, 2015 to Final Office Action mailed Feb. 4, 2015", 14 pgs.

"U.S. Appl. No. 12/950,273, Response filed Jun. 4, 2015 to Final Office Action mailed Feb. 4, 2015", 14 pgs.

"U.S. Appl. No. 14/109,368, Non Final Office Action mailed May 11, 2015", 6 pgs.

"U.S. Appl. No. 14/109,368, Response filed May 26, 2015 to Non-Final Office Action mailed Mar. 11, 2015", 12 pgs.

"U.S. Appl. No. 14/454,298, Notice of Allowance mailed Mar. 17, 2015", 8 pgs.

(56) References Cited

OTHER PUBLICATIONS

"U.S. Appl. No. 14/508,436, Preliminary Amendment filed Jan. 8, 2015", 7 pgs.
"U.S. Appl. No. 14/617,058, Preliminary Amendment filed Feb. 18, 2015", 8 pgs.
"Australian Application Serial No. 2010321745, Office Action mailed Jan. 12, 2015", 3 pgs.
"Australian Application Serial No. 2010321745, Response filed Apr. 24, 2015 to Office Action mailed Jan. 12, 2015", (18 pgs).
"Australian Application Serial No. 2010321812, Office Action mailed Jan. 12, 2015", 3 pgs.
"Australian Application Serial No. 2010321812, Response filed Apr. 24, 2015 to Office Action mailed Jan. 12, 2015", 19 pgs.
"Chinese Application Serial No. 201080052569.2 Response filed Nov. 7, 2014 to Non Final Office Action mailed Jun. 10, 2014", (W/ English Translation), 12 pgs.
"Chinese Application Serial No. 201080052569.2, Office Action mailed Jan. 28, 2015", (W/ English Translation), 5 pgs.
"Chinese Application Serial No. 201080052569.2, Response filed Mar. 26, 2015 to Office Action mailed Jan. 28, 2015", W/ English Claims, 10 pgs.
"Chinese Application Serial No. 201080052578.1, Office Action mailed Dec. 17, 2014", (W/ English Translation), 4 pgs.
"Chinese Application Serial No. 201080052578.1, Response filed Jan. 22, 2015 to Office Action mailed Dec. 17, 2014", (W/ English Translation), 8 pgs.
"Chinese Application Serial No. 201080052578.1, Response filed Aug. 12, 2014 to Office Action mailed Apr. 1, 2014", W/ English Claims, 13 pgs.
"Chinese Application Serial No. 201080052580.9, Response filed Aug. 14, 2014 to Office Action mailed Apr. 3, 2014", W/ English Claims, 12 pgs.
"Chinese Application Serial No. 201080052583.2, Office Action mailed Dec. 24, 2014", (W/ English Translation), 4 pgs.
"Chinese Application Serial No. 201080052583.2, Response filed Sep. 26, 2014 to Office Action mailed Mar. 14, 2014", (W/ English Translation of Claims), 10 pgs.
"U.S. Appl. No. 12/950,061, Final Office Action mailed Jul. 15, 2013", 7 pgs.
"U.S. Appl. No. 12/950,061, Non Final Office Action mailed Feb. 7, 2013", 7 pgs.
"U.S. Appl. No. 12/950,061, Notice of Allowance mailed Oct. 1, 2013", 6 pgs.
"U.S. Appl. No. 12/950,061, Preliminary Amendment filed Feb. 8, 2011", 3 pgs.
"U.S. Appl. No. 12/950,061, Response filed Jun. 7, 2013 to Non Final Office Action mailed Feb. 7, 2013", 14 pgs.
"U.S. Appl. No. 12/950,061, Response filed Sep. 16, 2013 to Final Office Action mailed Jul. 15, 2013", 13 pgs.
"U.S. Appl. No. 12/950,097, Final Office Action mailed Dec. 10, 2013", 6 pgs.
"U.S. Appl. No. 12/950,097, Non Final Office Action mailed Feb. 15, 2013", 8 pgs.
"U.S. Appl. No. 12/950,097, Non Final Office Action mailed Aug. 6, 2013", 6 pgs.
"U.S. Appl. No. 12/950,097, Notice of Allowance mailed Feb. 2, 2014", 5 pgs.
"U.S. Appl. No. 12/950,097, Notice of Allowance mailed Jul. 9, 2014", 5 pgs.
"U.S. Appl. No. 12/950,097, Preliminary Amendment filed Feb. 7, 2011", 3 pgs.
"U.S. Appl. No. 12/950,097, Response filed Mar. 10, 2014 to Final Office Action mailed Dec. 10, 2013", 13 pgs.
"U.S. Appl. No. 12/950,097, Response filed Jun. 17, 2013 to Non Final Office Action mailed Feb. 15, 2013", 15 pgs.
"U.S. Appl. No. 12/950,097, Response filed Nov. 6, 2013 to Non Final Office Action mailed Aug. 6, 2013", 14 pgs.
"U.S. Appl. No. 12/950,114, Final Office Action mailed Jul. 15, 2013", 6 pgs.
"U.S. Appl. No. 12/950,114, Non Final Office Action mailed Feb. 6, 2014", 6 pgs.
"U.S. Appl. No. 12/950,114, Non Final Office Action mailed Mar. 7, 2013", 6 pgs.
"U.S. Appl. No. 12/950,114, Notice of Allowance mailed Jun. 16, 2014", 5 pgs.
"U.S. Appl. No. 12/950,114, Preliminary Amendment filed Feb. 8, 2011", 3 pgs.
"U.S. Appl. No. 12/950,114, Response filed May 6, 2014 to Non-Final Office Action mailed Feb. 6, 2014", 7 pgs.
"U.S. Appl. No. 12/950,114, Response filed Jun. 7, 2013 to Non Final Office Action mailed Mar. 7, 2013", 8 pgs.
"U.S. Appl. No. 12/950,114, Response filed Sep. 16, 2013 to Final Office Action mailed Jul. 15, 2013", 8 pgs.
"U.S. Appl. No. 12/950,154, Examiner Interview Summary mailed Aug. 19, 2014", 3 pgs.
"U.S. Appl. No. 12/950,154, Final Office Action mailed Aug. 8, 2013", 7 pgs.
"U.S. Appl. No. 12/950,154, Non Final Office Action mailed Feb. 25, 2014", 6 pgs.
"U.S. Appl. No. 12/950,154, Non Final Office Action mailed Mar. 15, 2013", 8 pgs.
"U.S. Appl. No. 12/950,154, Notice of Allowance mailed Oct. 10, 2014", 6 pgs.
"U.S. Appl. No. 12/950,154, Preliminary Amendment filed Feb. 7, 2011", 4 pgs.
"U.S. Appl. No. 12/950,154, Response filed Jun. 17, 2013 to Non Final Office Action mailed Mar. 15, 2013", 15 pgs.
"U.S. Appl. No. 12/950,154, Response filed Aug. 25, 2014 to Non-Final Office Action mailed Feb. 25, 2014", 18 pgs.
"U.S. Appl. No. 12/950,154, Response filed Oct. 8, 2013 to Final Office Action mailed Aug. 8, 2013", 18 pgs.
"U.S. Appl. No. 12/950,183, Examiner Interview Summary mailed Feb. 13, 2014", 3 pgs.
"U.S. Appl. No. 12/950,183, Final Office Action mailed Oct. 30, 2012", 16 pgs.
"U.S. Appl. No. 12/950,183, Non Final Office Action mailed May 29, 2012", 10 pgs.
"U.S. Appl. No. 12/950,183, Non Final Office Action mailed Oct. 11, 2013", 12 pgs.
"U.S. Appl. No. 12/950,183, Notice of Allowance mailed Feb. 19, 2014", 5 pgs.
"U.S. Appl. No. 12/950,183, Notice of Allowance mailed Jun. 6, 2014", 7 pgs.
"U.S. Appl. No. 12/950,183, Preliminary Amendment filed Feb. 8, 2011", 4 pgs.
"U.S. Appl. No. 12/950,183, Response filed Jul. 13, 2014 to Non Final Office Action mailed Oct. 11, 2013", 11 pgs.
"U.S. Appl. No. 12/950,183, Response filed Apr. 30, 2013 to Final Office Action mailed Oct. 30, 2012", 11 pgs.
"U.S. Appl. No. 12/950,183, Response filed May 11, 2012 to Restriction Requirement mailed Apr. 13, 2012", 2 pgs.
"U.S. Appl. No. 12/950,183, Response filed Aug. 28, 2012 to Non Final Office Action mailed May 29, 2012", 10 pgs.
"U.S. Appl. No. 12/950,183, Restriction Requirement mailed Apr. 13, 2012", 8 pgs.
"U.S. Appl. No. 12/950,183, Supplemental Amendment filed Feb. 7, 2014", 8 pgs.
"U.S. Appl. No. 12/950,230, Examiner Interview Summary mailed Nov. 12, 2014", 3 pgs.
"U.S. Appl. No. 12/950,230, Final Office Action mailed Jan. 11, 2013", 10 pgs.
"U.S. Appl. No. 12/950,230, Non Final Office Action mailed Jul. 17, 2014", 10 pgs.
"U.S. Appl. No. 12/950,230, Non Final Office Action mailed Aug. 2, 2012", 9 pgs.
"U.S. Appl. No. 12/950,230, Preliminary Amendment filed Feb. 8, 2011", 3 pgs.
"U.S. Appl. No. 12/950,230, Response filed Apr. 11, 2013 to Final Office Action mailed Jan. 11, 2013", 10 pgs.
"U.S. Appl. No. 12/950,230, Response filed Nov. 2, 2012 to Non Final Office Action mailed Aug. 2, 2012", 8 pgs.

(56) References Cited

OTHER PUBLICATIONS

"U.S. Appl. No. 12/950,230, Response filed Nov. 17, 2014 to Non-Final Office Action mailed Jul. 17, 2014", 15 pgs.
"U.S. Appl. No. 12/950,273, Final Office Action mailed Nov. 6, 2012", 9 pgs.
"U.S. Appl. No. 12/950,273, Non Final Office Action mailed Apr. 13, 2012", 15 pgs.
"U.S. Appl. No. 12/950,273, Non Final Office Action mailed Apr. 25, 2014", 12 pgs.
"U.S. Appl. No. 12/950,273, Preliminary Amendment filed Feb. 8, 2011", 3 pgs.
"U.S. Appl. No. 12/950,273, Response filed Mar. 6, 2013 to Final Office Action mailed Nov. 6, 2012", 10 pgs.
"U.S. Appl. No. 12/950,273, Response filed Jul. 12, 2012 to Non Final Office Action mailed Apr. 13, 2012", 12 pgs.
"U.S. Appl. No. 12/950,273, Response filed Oct. 24, 2014 to Non-Final Office Action mailed Apr. 25, 2014", 14 pgs.
"U.S. Appl. No. 12/950,306, Final Office Action mailed Nov. 26, 2012", 9 pgs.
"U.S. Appl. No. 12/950,306, Non Final Office Action mailed Jun. 14, 2012", 11 pgs.
"U.S. Appl. No. 12/950,306, Notice of Allowance mailed May 28, 2013", 9 pgs.
"U.S. Appl. No. 12/950,306, Notice of Allowance mailed Apr. 13, 2013", 9 pgs.
"U.S. Appl. No. 12/950,306, Preliminary Amendment filed Feb. 8, 2011", 7 pgs.
"U.S. Appl. No. 12/950,306, Response filed Apr. 30, 2013 to Final Office Action mailed Nov. 26, 2012", 15 pgs.
"U.S. Appl. No. 12/950,306, Response filed Sep. 13, 2012 to Non Final Office Action mailed Jun. 14, 2012", 11 pgs.
"U.S. Appl. No. 12/950,355, Final Office Action mailed Mar. 12, 2013", 15 pgs.
"U.S. Appl. No. 12/950,355, Non Final Office Action mailed Jul. 29, 2014", 9 pgs.
"U.S. Appl. No. 12/950,355, Non Final Office Action mailed Aug. 13, 2012", 16 pgs.
"U.S. Appl. No. 12/950,355, Notice of Allowance mailed Dec. 9, 2014", 6 pgs.
"U.S. Appl. No. 12/950,355, Response filed Jan. 14, 2013 to Non Final Office Action mailed Aug. 13, 2012", 17 pgs.
"U.S. Appl. No. 12/950,355, Response filed Jul. 12, 2013 to Final Office Action mailed Mar. 12, 2013", 20 pgs.
"U.S. Appl. No. 12/950,355, Response filed Oct. 28, 2014 to Non-Final Office Action mailed Jul. 29, 2014", 21 pgs.
"U.S. Appl. No. 14/143,883, Non Final Office Action mailed Aug. 4, 2014", 6 pgs.
"U.S. Appl. No. 14/143,883, Notice of Allowance mailed Jan. 26, 2015", 6 pgs.
"U.S. Appl. No. 14/143,883, Response filed Dec. 4. 2014 to Non-Final Office Action mailed Aug. 4, 2014", 9 pgs.
"U.S. Appl. No. 14/453,301, Preliminary Amendment filed Oct. 6, 2014", 8 pgs.
"U.S. Appl. No. 14/454,298, Preliminary Amendment filed Sep. 18, 2014", 7 pgs.
"Chinese Application Serial No. 201080020717.2, Office Action mailed Jan. 9, 2014", (W/English Translation), 11 pgs.
"Chinese Application Serial No. 201080052569.2, Office Action mailed Apr. 25, 2014", (W/English Translation), 17 pgs.
"Chinese Application Serial No. 201080052578.1, Office Action mailed Apr. 1, 2014", (W/ English Translation), 11 pgs.
"Chinese Application Serial No. 201080052580.9, Office Action mailed Apr. 3, 2014", w/English Translation, 18 pgs.
"Chinese Application Serial No. 201080052580.9, Office Action mailed Nov. 25, 2014", (W/ English Translation), 18 pgs.
"Chinese Application Serial No. 201080052583.2, Office Action mailed Mar. 14, 2014", (W// English Translation), 9 pgs.
"European Application Serial No. 10832277.7, Office Action mailed Jun. 27, 2012", 2 pgs.
"European Application Serial No. 10832285.0, Office Action mailed Jun. 27, 2012", 2 pgs.
"International Application Serial No. PCT/US2010/057426, International Preliminary Report on Patentability mailed May 22, 2012", 9 pgs.
"International Application Serial No. PCT/US2010/057426, International Search Report and Written Opinion mailed Jan. 24, 2011", 10 pgs.
"International Application Serial No. PCT/US2010/057440, International Preliminary Report on Patentability mailed May 22, 2012", 7 pgs.
"International Application Serial No. PCT/US2010/057440, International Search Report and Written Opinion mailed Feb. 7, 2011", 8 pgs.
"International Application Serial No. PCT/US2010/057456, International Preliminary Report on Patentability mailed May 22, 2012", 6 pgs.
"International Application Serial No. PCT/US2010/057456, International Search Report and Written Opinion mailed Jan. 14, 2011", 7 pgs.
"International Application Serial No. PCT/US2010/057471, International Preliminary Report on Patentability mailed May 31, 2012", 7 pgs.
"International Application Serial No. PCT/US2010/057471, International Search Report mailed Jan. 18, 2011", 2 pgs.
"International Application Serial No. PCT/US2010/057471, Written Opinion mailed Jan. 18, 2011", 5 ogs.
"International Application Serial No. PCT/US2010/057475, International Preliminary Report on Patentability mailed May 22, 2012", 6 pgs.
"International Application Serial No. PCT/US2010/057475, International Search Report mailed Jan. 18, 2011", 8 pgs.
"International Application Serial No. PCT/US2010/057475, Written Opinion mailed Jan. 18, 2011", 5 pgs.
"International Application Serial No. PCT/US2010/057483, International Preliminary Report on Patentability mailed May 22, 2012", 6 pgs.
"International Application Serial No. PCT/US2010/057483, International Search Report and Written Opinion mailed Feb. 2, 2011", 7 pgs.
"International Application Serial No. PCT/US2010/057498, International Preliminary Report on Patentability mailed May 22, 2012", 5 pgs.
"International Application Serial No. PCT/US2010/057498, International Search Report mailed Jan. 24, 2011", 2 pgs.
"International Application Serial No. PCT/US2010/057498, Written Opinion mailed Jan. 24, 2011", 4 pgs.
"International Application Serial No. PCT/US2010/057500, International Preliminary Report on Patentability mailed May 31, 2012", 8 pgs.
"International Application Serial No. PCT/US2010/057500, International Search Report mailed Jan. 27, 2011", 2 pgs.
"International Application Serial No. PCT/US2010/057500, Written Opinion mailed Jan. 27, 2011", 6 pgs.
"Riddle Memorial Hospital, Medial, PA 19063 Operative Report. Surgeon: Peter F Sharkey M.D.", Right Knee, Medial tibial plateau; A cannulated bone biopsy needle was placed into the bone under fluoroscopic guidance;, Implant used: Stryker Orthopedics Hydroset (Bone Substitute Material); Surgeon also expressed difficulty in injecting the bone substitute, (May 12, 2008), 2 pgs.
"SPU Operative Report. Surgen: Steven B Cohen, M.D.", Treatment of the central medial tibial plateau; A guide pin was inserted into the medial tibial plateau;, An endo button drill bit was used to expand the drill hole; One cubic centimeter (cc) of cement was inserted into the bone; A second drill hole was made from below, and a second cc was inserted into the bone., (Nov. 10, 2008), 4 pgs.

(56) References Cited

OTHER PUBLICATIONS

"SPU Operative Report: Surgen Steven B Cohen, M.D.", an Anterior Cruciate Ligament (ACL) portal-creation device was repurposed for this surgery; The tibial probe was placed on the medial femoral condyle, with the tunnel guide secured proximally on the thigh;, The surgeon expressed difficulty in positioning and stabilizing the guide; A cannulated pin was placed through the tunnel guide and placed distally into the medial femoral condyle; No implant was injected into the bone., (Oct. 27, 2008), 4 pgs.

"U.S. Appl. No. 12/950,230, Notice of Allowance mailed Oct. 7, 2015", 5 pgs.

"U.S. Appl. No. 12/950,230, Response filed Jul. 15, 2015 to Non Final Office Action mailed Apr. 15, 2015", 16 pgs.

"U.S. Appl. No. 12/950,273, Non Final Office Action mailed Nov. 24, 2015", 10 pgs.

"U.S. Appl. No. 12/950,273, Response filed Dec. 29, 2015 to Non Final Office Action mailed Nov. 24, 2015", 11 pgs.

"U.S. Appl. No. 14/109,368, Final Office Action mailed Jul. 9, 2015", 10 pgs.

"U.S. Appl. No. 14/109,368, Notice of Allowance mailed Nov. 24, 2015", 10 pgs.

"U.S. Appl. No. 14/109,368, Response filed Nov. 9, 2015 to Final Office Action mailed Jul. 9, 2015", 17 pgs.

"U.S. Appl. No. 14/453,301, Non Final Office Action mailed Sep. 23, 2015", 17 pgs.

"U.S. Appl. No. 14/453,301, Response filed Dec. 23, 2015 to Non Final Office Action mailed Sep. 23, 2015", 15 pgs.

"U.S. Appl. No. 14/454,298, Notice of Allowance mailed Jul. 1, 2015", 6 pgs.

"U.S. Appl. No. 14/508,436, Non Final Office Action mailed Sep. 11, 2015", 7 pgs.

"U.S. Appl. No. 14/508,436, Notice of Allowance mailed Feb. 4, 2016", 5 pgs.

"U.S. Appl. No. 14/508,436, Response filed Dec. 11, 2015 to Non Final Office Action mailed Sep. 11, 2015", 10 pgs.

"U.S. Appl. No. 14/724,160, Non Final Office Action mailed Sep. 11, 2015", 5 pgs.

"U.S. Appl. No. 14/724,160, Notice of Allowance mailed Feb. 4, 2016", 5 pgs.

"U.S. Appl. No. 14/724,160, Preliminary Amendment filed Jun. 17, 2015", 8 pgs.

"U.S. Appl. No. 14/724,160, Response filed Nov. 25, 2015 to Non Final Office Action mailed Sep. 11, 2015", 8 pgs.

U.S. Appl. No. 14/454,298, filed Aug. 7, 2014, Method for Treating Joint Pain and Associated Instruments.

U.S. Appl. No. 14/724,160, filed May 28, 2015, Method for Treating Joint Pain and Associated Instruments.

U.S. Appl. No. 12/950,273, filed Nov. 19, 2010, Implantable Device for Subchondral Treatment of Joint Pain.

U.S. Appl. No. 12/950,230, filed Nov. 19, 2010, Instruments for Targeting a Joint Defect.

U.S. Appl. No. 14/617,058, filed Feb. 9, 2015, Subchondral Treatment of Joint Pain.

U.S. Appl. No. 14/508,436, filed Oct. 7, 2014, Coordinate Mapping System for Joint Treatment.

U.S. Appl. No. 14/109,368, filed Dec. 17, 2013, Implantable Devices for Subchondral Treatment of Joint Pain.

U.S. Appl. No. 14/453,301, filed Aug. 6, 2014, Bone-Derived Implantable Devices for Subchondral Treatment of Joint Pain.

* cited by examiner

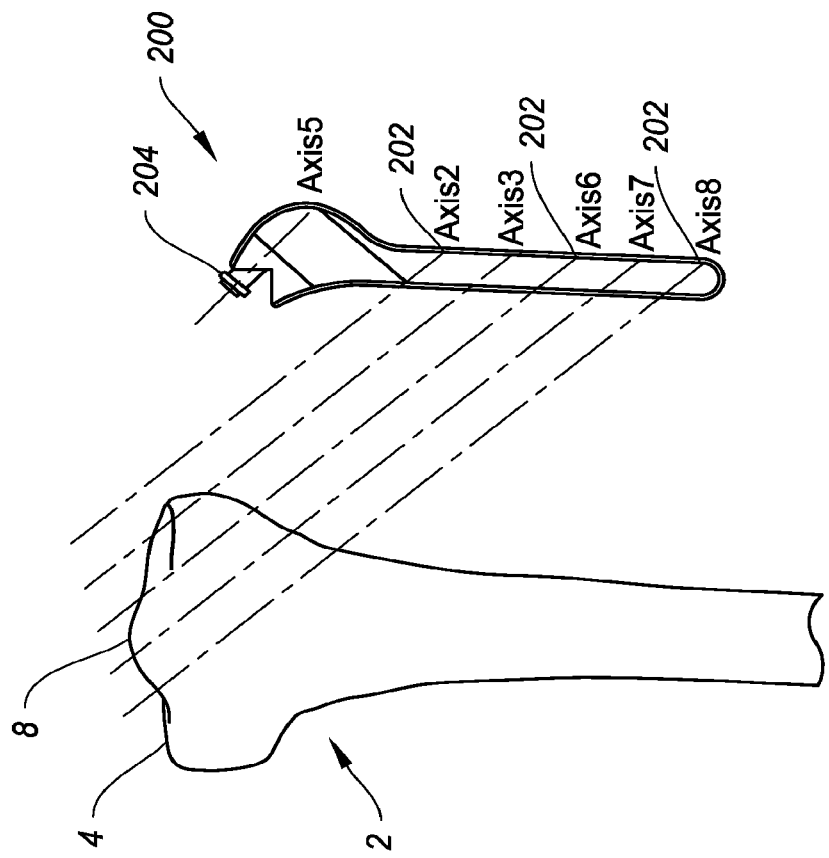
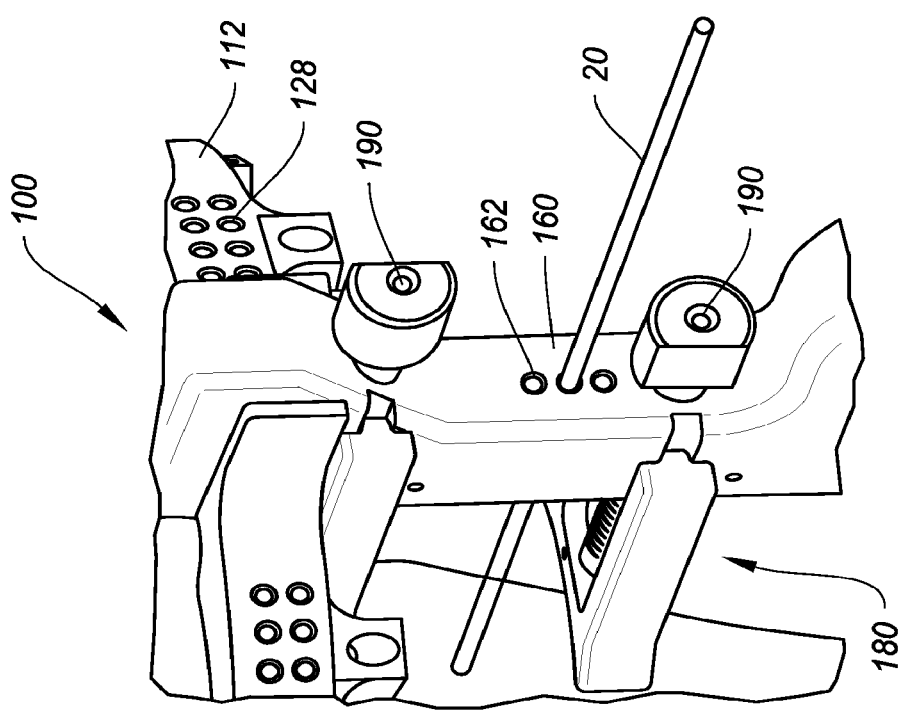
FIG. 10
FIG. 9

NAVIGATION AND POSITIONING INSTRUMENTS FOR JOINT REPAIR

CROSS-REFERENCE TO RELATED TO APPLICATIONS

This application is a continuation of U.S. patent application Ser. No. 14/143,883, filed on Dec. 30, 2013, which application is a continuation of U.S. patent application Ser. No. 12/950,061, now U.S. Pat. No. 8,617,166, filed Nov. 19, 2010 and entitled "NAVIGATION AND POSITIONING INSTRUMENTS FOR JOINT REPAIR", which claims priority to U.S. Provisional No. 61/377,313 filed Aug. 26, 2010, and entitled "NAVIGATION AND POSITIONING INSTRUMENTS FOR JOINT REPAIR AND METHODS OF USE," and U.S. Provisional No. 61/263,170 filed Nov. 20, 2009, and entitled "METHOD FOR TREATING JOINT PAIN AND ASSOCIATED INSTRUMENTS," all of which are herein incorporated by reference in their entirety.

This application also relates to U.S. patent application Ser. No. 12/950,355, filed Nov. 19, 2010 and entitled "SUBCHONDRAL TREATMENT OF JOINT PAIN," the content of which is herein incorporated in its entirety by reference.

FIELD

The present invention relates to tools for the surgical treatment of joints, and more particularly to instruments and associated methods for the surgical repair and treatment of bone tissue at these joints. Even more particularly, the present invention relates to navigation and positioning instruments for locating and positioning a device in an area near a bone defect using anatomical landmarks.

BACKGROUND

Human joints, in particular the knee, hip and spine, are susceptible to degeneration from disease, trauma, and long-term repetitive use that eventually lead to pain. Knee pain, for example, is the impetus for a wide majority of medical treatments and associated medical costs. The most popular theory arising from the medical community is that knee pain results from bone-on-bone contact or inadequate cartilage cushioning. These conditions are believed to frequently result from the progression of osteoarthritis, which is measured in terms of narrowing of the joint space. Therefore, the severity of osteoarthritis is believed to be an indicator or precursor to joint pain. Most surgeons and medical practitioners thus base their treatments for pain relief on this theory. For example, the typical treatment is to administer pain medication, or more drastically, to perform some type of joint resurfacing or joint replacement surgery.

However, the severity of osteoarthritis, especially in the knee, has been found to correlate poorly with the incidence and magnitude of knee pain. Because of this, surgeons and medical practitioners have struggled to deliver consistent, reliable pain relief to patients especially if preservation of the joint is desired.

Whether by external physical force, disease, or the natural aging process, structural damage to bone can cause injury, trauma, degeneration or erosion of otherwise healthy tissue. The resultant damage can be characterized as a bone defect that can take the form of a fissure, fracture, lesion, edema, tumor, or sclerotic hardening, for example. Particularly in joints, the damage may not be limited to a bone defect, and may also include cartilage loss (especially articular cartilage), tendon damage, and inflammation in the surrounding area.

Patients most often seek treatment because of pain and deterioration of quality of life attributed to the osteoarthritis. The goal of surgical and non-surgical treatments for osteoarthritis is to reduce or eliminate pain and restore joint function. Both non-surgical and surgical treatments are currently available for joint repair.

Non-surgical treatments include weight loss (for the overweight patient), activity modification (low impact exercise), quadriceps strengthening, patellar taping, analgesic and anti-inflammatory medications, and with corticosteroid and/or viscosupplements. Typically, non-surgical treatments, usually involving pharmacological intervention such as the administration of non-steroidal anti-inflammatory drugs or injection of hyaluronic acid-based products, are initially administered to patients experiencing relatively less severe pain or joint complications. However, when non-surgical treatments prove ineffective, or for patients with severe pain or bone injury, surgical intervention is often necessary.

Surgical options include arthroscopic partial meniscectomy and loose body removal. Most surgical treatments conventionally employ mechanical fixation devices such as screws, plates, staples, rods, sutures, and the like are commonly used to repair damaged bone. These fixation devices can be implanted at, or around, the damaged region to stabilize or immobilize the weakened area, in order to promote healing and provide support. Injectable or fillable hardening materials such as bone cements, bone void fillers, or bone substitute materials are also commonly used to stabilize bone defects.

High tibial osteotomy (HTO) or total knee arthroplasty (TKA) is often recommended for patients with severe pain associated with osteoarthritis, especially when other non-invasive options have failed. Both procedures have been shown to be effective in treating knee pain associated with osteoarthritis.

However, patients only elect HTO or TKA with reluctance. Both HTO and TKA are major surgical interventions and may be associated with severe complications. HTO is a painful procedure that may require a long recovery. TKA patients often also report the replaced knee lacks a "natural feel" and have functional limitations. Moreover, both HTO and TKA have limited durability. Accordingly, it would be desirable to provide a medical procedure that addresses the pain associated with osteoarthritis and provides an alternative to a HTO or TKA procedure.

In current practice, surgeons typically "eyeball" (i.e., visually estimate) the target site on a bone to be repaired. Most conventional targeting and location methods are relatively crude and provide little guidance to a surgeon during the actual surgical procedure. Accordingly, it would be desirable to provide methods and instruments in which the area near a bone defect can be easily located and provide a reference framework that can be used in a surgical procedure irrespective of the approach. Furthermore, in some situations where pinpoint accuracy is not critical or necessary, a navigation system that can indicate an area sufficiently near the bone defect in a quick and reliable manner would be highly beneficial to the clinician.

Accordingly, it is desirable to provide instruments that allow fast, easy, and repeatable navigation to, and positioning of devices in, an area sufficiently near a bone defect to be treated. It is further desirable to provide instruments that do not obstruct access to the working area around the target site, and allow as clear a view as possible for the clinician.

SUMMARY

The present disclosure provides instruments for locating and positioning a device in an area sufficiently near a bone defect using anatomical landmarks. The instruments allow the surgeon to navigate to the area around the bone defect quickly and easily, while also facilitating proper insertion of a device into an appropriate area near the defect.

In one exemplary embodiment, an instrument for controlled delivery of a device to a target area near a defect of a bone is provided. The instrument comprises a guide frame having a plurality of device portals, each portal defining a trajectory. The guide frame further includes visual markers for aligning the guide frame to an anatomical landmark on the bone to be treated. The instrument also includes a holder for releasable attachment with the guide frame. Each device portal is configured to provide accurate and controlled delivery of the device to the target area. In one example, the markers are radiopaque, and are visualized through fluoroscopy.

In another exemplary embodiment, a method for treating a target area near a bone defect is provided. The method includes the steps of providing an instrument for controlled delivery of a device to the target area near the bone defect, the instrument including a guide frame having a plurality of device portals, each portal defining a trajectory, the frame further including visual markers for aligning the guide frame to an anatomical landmark on the bone to be treated, a holder for releasable attachment with the guide frame, and wherein each device portal is configured to provide accurate and controlled delivery of the device to the target area, and introducing a device through the device portal of the guide frame and to the target area. The device could be a pin, drill bit, an implantable device, or an insertion tool, for example.

BRIEF DESCRIPTION OF THE DRAWINGS

The accompanying drawings, which are incorporated in and constitute a part of this specification, illustrate several embodiments of the disclosure and together with the description, serve to explain the principles of the disclosure.

FIG. 9 is an enlarged view of the main body of the instrument of FIG. 8;

FIG. 10 shows a distal guide that can optionally be used with the instrument of FIG. 3 oriented relative to a partial tibia;

DESCRIPTION OF THE EMBODIMENTS

Figure 1:
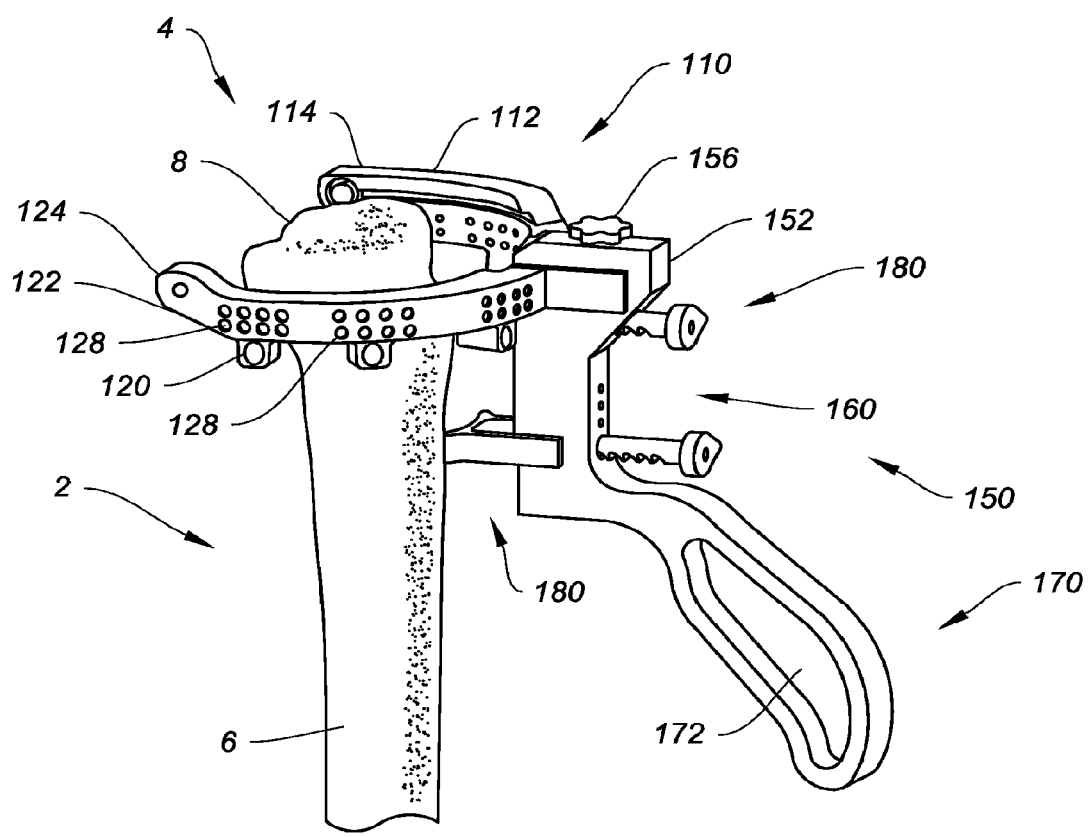
FIG. 1 is a perspective view of an exemplary embodiment of a navigation and positioning instrument of the present invention shown in use with a partial tibia.

The present disclosure provides a methodology, devices and instruments for diagnosing and treating joint pain to restore natural joint function and preserving, as much as possible, the joint's articular and cartilage surface. Treatments through the joint that violate the articular and cartilage surface often weaken the bone and have unpredictable results. Rather than focusing on treatment of pain through the joint, the embodiments diagnose and treat pain at its source in the subchondral region of a bone of a joint to relieve the pain. Applicants have discovered that pain associated with joints, especially osteoarthritic joints, can be correlated to bone defects or changes at the subchondral level rather than, for example, the severity of osteoarthritic progression or defects at the articular surface level. In particular, bone defects, such as bone marrow lesions, edema, fissures, fractures, hardened bone, etc. near the joint surface lead to a mechanical disadvantage and abnormal stress distribution in the periarticular bone, which may cause inflammation and generate pain. By altering the makeup of the periarticular bone (which may or may not be sclerotic) in relation to the surrounding region, it is possible to change the structural integrity of the affected bone and restore normal healing function, thus leading to a resolution of the inflammation surrounding the defect.

Applicants have discovered that treatment of the bone by mechanical and biological means to restore the normal physiologic stress distribution, and restore the healing balance of the bone tissue at the subchondral level, is a more effect way of treating pain than conventional techniques. That is, treatment can be effectively achieved by mechanically strengthening or stabilizing the defect, and biologically initiating or stimulating a healing response to the defect. Accordingly, the present disclosure provides methods, devices, and systems for a subchondral procedure This procedure and its associated devices, instruments, etc. are also marketed under the registered trademark name of SUBCHONDROPLASTY™. The SUBCHONDROPLASTY™ procedure is a response to a desire for an alternative to patients facing partial or total knee replacement.

In general, the SUBCHONDROPLASTY™ or SCP™ technique is intended to both strengthen the bone and stimulate the bone. In SCP™, bone fractures or non-unions are stabilized, integrated or healed, which results in reduction of a bone defect, such as a bone marrow lesion or edema. In addition, SCP™ restores or alters the distribution of forces in a joint to thereby relieve pain. SCP™ can be performed arthroscopically or percutaneously to treat pain by stabilizing chronic stress fracture, resolving any chronic bone marrow lesion or edema, and preserving, as much as possible, the articular surfaces of the joint. SUBCHONDROPLASTY™ generally comprises evaluating a joint, for example, by taking an image of the joint, detecting the presence of one or more subchondral defects, diagnosing, which of these subchondral defects is the source of pain, and determining an extent of treatment for the subchondral defect. The present technique is particularly suited for treating chronic defects or injuries, where the patient's natural healing response has not resolved the defect. It should be noted, however, that the technique is equally applicable to treatment of defects in the subchondral region of bone where the defect is due to an acute injury or from other violations. The present disclosure provides several exemplary treatment modalities for SCP™ for the different extents of treatment needed. Accordingly, a medical practitioner may elect to use the techniques and devices described herein to subchondrally treat any number of bone defects, as he deems appropriate.

In some embodiments, detection and identification of the relevant bone marrow lesion or bone marrow edema (BML or BME) can be achieved by imaging, e.g., magnetic resonance imaging (MRI), X-ray, manual palpation, chemical or biological assay, and the like. A T1-weighted MRI can be used to detect sclerotic bone, for example. Another example is that a T2-weighted MRI can be used to detect lesions, edemas, and cysts. X-ray imaging may be suitable for early-stage as well as end-stage arthritis. From the imaging, certain defects may be identified as the source of pain. In general, defects that are associated with chronic injury and chronic deficit of healing are differentiated from defects that result, e.g., from diminished bone density. SCP™ treatments are appropriate for a BML or BME that may be characterized as a bone defect that is chronically unable to heal (or remodel) itself, which may cause a non-union of the bone, stress or insufficiency fractures, and perceptible pain. Factors considered may include, among other things, the nature of the defect, size of the defect, location of the defect, etc. For example, bone defects at the edge near the articular surface of periphery of a joint may be often considered eligible for treatment due to edge-loading effects as well as the likelihood of bone hardening at these locations. A bone defect caused by an acute injury would generally be able to heal itself through the patient's own natural healing process. However, in such situations where the bone defect is due to an acute injury and either the defect does not heal on its own, or the medical practitioner decides that the present technique is appropriate, SCP™ treatment can be administered on acute stress fractures, BML or BME, or other subchondral defects, as previously mentioned.

According to the embodiments, the SCP™ treatment may continue after surgery. In particular, the patient may be monitored for a change in pain scores, or positive change in function. For example, patients are also checked to see when they are able to perform full weight-bearing activity and when they can return to normal activity. Of note, if needed, the SCP™ procedure can be completely reversed in the event that a patient requires or desires a joint replacement or other type of procedure. The SCP™ treatment may also be performed in conjunction with other procedures, such as cartilage resurfacing, regeneration or replacement, if desired.

The present disclosure provides a number of treatment modalities, as associated devices, instruments and related methods of use for performing SUBCHONDROPLASTY™. These treatment modalities may be used alone or in combination.

In one treatment modality, the subchondral bone in the region of the bone marrow lesion or defect can be strengthened by introduction of a hardening material, such as a bone substitute, at the site. The bone substitute may be an injectable calcium phosphate ensconced in an optimized carrier material. In SCP™, the injected material may also serve as a bone stimulator that reinvigorates the desired acute bone healing activity.

For example, polymethylmethacrylate (PMMA) or calcium phosphate (CaP) cement injections can be made at the defect site. PMMA injection may increase the mechanical strength of the bone, allowing it to withstand greater mechanical stresses. CaP cement injection may also increase the mechanical strength of the bone, while also stimulating the localized region for bone fracture repair. In one embodiment, the injection can be made parallel to the joint surface. In another embodiment, the injection can be made at an angle to the joint surface. In yet another embodiment, the injection can be made below a bone marrow lesion.

In another treatment modality, the subchondral bone region can be stimulated to trigger or improve the body's natural healing process. For example, in one embodiment of this treatment modality, one or more small holes may be drilled at the region of the defect to increase stimulation (e.g., blood flow, cellular turnover, etc.) and initiate a healing response leading to bone repair. In another embodiment, after holes are drilled an osteogenic, osteoinductive, or osteoconductive agent may be introduced to the site. Bone graft material, for example, may be used to fill the hole. This treatment modality may create a better load-supporting environment leading to long term healing. Electrical or heat stimulation may also be employed to stimulate the healing process of a chronically injured bone. Chemical, biochemical and/or biological stimulation may also be employed in SCP™. For instance, stimulation of bone tissue in SCP™ may be enhanced via the use of cytokines and other cell signaling agents to trigger osteogenesis, chondrogenesis, and/or angiogenesis to perhaps reverse progression of osteoarthritis.

In yet another treatment modality, an implantable device may be implanted into the subchondral bone to provide mechanical support to the damaged or affected bone region, such as where an insufficiency fracture or stress fracture has occurred. The implant may help create a better load distribution in the subchondral region. In the knees, the implant may support tibio-femoral compressive loads. In addition, the implant may mechanically integrate sclerotic bone with the surrounding healthy bone tissue. The implants may be place in cancellous bone, through sclerotic bone, or under sclerotic bone at the affected bone region. The implant may also be configured as a bi-cortical bone implant. In one embodiment, one side of the implant can be anchored to the peripheral cortex to create a cantilever beam support (i.e., a portion of the implant is inserted into bone but the second end stays outside or near the outer surface of the bone). The implant may be inserted using a guide wire. In one example, the implant may be inserted over a guide wire. In another example, the implant may be delivered through a guide instrument.

The implant may further be augmented with a PMMA or CaP cement injection, other biologic agent, or an osteoconductive, osteoinductive and/or osteogenic agent. The augmentation material may be introduced through the implant, around the implant, and/or apart from the implant but at the affected bone region, such as into the lower region of a bone marrow lesion or below the lesion. For example, the implant may act as a portal to inject the augmentation material into the subchondral bone region.

While each of the above-mentioned treatment modalities may be administered independ of one another, it is contemplated that any combination of these modalities may be applied together and in any order so desired, depending on the severity or stage of development of the bone defect(s). Accordingly, the present disclosure also provides suitable implantable fixation devices for the surgical treatment of these altered bone regions or bone defects, especially at the subchondral level. Applicants have also discovered devices and instruments that can be use in combination with cements or hardening materials commonly used to repair damaged bone by their introduction into or near the site of damage, either to create a binding agent, cellular scaffold or mechanical scaffold for immobilization, regeneration or remodeling of the bone tissue.

In general, the embodiments relate to instruments and associated methods for the surgical treatment of a joint, and particularly to a bone defect at that joint region. More specifically, the embodiments relate to instruments for navigating and positioning devices into an area sufficiently near a defect of the joint. Even more specifically, the instruments and associated methods for use are suitable for the repair of a tibial bone of a knee joint.

In a healthy joint such as a tibio-femoral joint, the compressive load between the contact bones (i.e., the femur and the tibia) is properly distributed, thus keeping the contact stresses in the cartilage to a reasonably low level. As the cartilage starts to wear out locally, the tibio-femoral contact area reduces and starts to get localized at the site of the cartilage defect. The localization of the stresses may also occur due to varus or valgus deformity. Sometimes, the condition may occur because of osteoporosis, where bone becomes weak and is no longer able to support normal loads. This condition leads to higher localized contact stresses in the cartilage, and the subchondral region below the cartilage. Once the stresses reach beyond a certain threshold level, it leads to defects like bone marrow lesions and edema, and perhaps generates knee pain. If the problem persists, the high contact stresses can lead to sclerotic bone formation as well. The presence of sclerotic bone can compromise vascularization of the local area, and also create a mechanical mismatch in the bone tissue. This mismatch may start to expedite degeneration of all parts of the joint leading to increased levels of osteoarthritis.

With this understanding, applicants have discovered that pain associated with osteoarthritic joints can be correlated to bone defects or changes at the subchondral level. In particular, bone defects such as bone marrow lesions, edema, fissures, fractures, etc. near the joint surface lead to abnormal stress distribution in the periarticular bone, which may or may not cause inflammation and generate pain. By altering the makeup of the periarticular bone (which may or may not be sclerotic) in relation to the surrounding region, it is possible to change the structural integrity of the affected bone, leading to a resolution of the inflammation. Applicants have discovered that treatment of the bone in an effort to alter the structural makeup of the affected periarticular bone leads to reduced inflammation and pain. Over time, normal physiologic stress distribution can be achieved, and mechanical congruity restored, thereby resulting in healing of the inflammation and reduction or elimination of pain.

As previously mentioned, there is a need for surgical instruments that allow fast, easy, and repeatable navigation to, and proper positioning of devices into, a generalized area sufficiently near a bone defect to be treated. Applicants have discovered instruments that are particularly suitable for accessing certain areas of the bone within the range of about 2-15 mm from the bone surface, and more commonly about 5-10 mm from the bone surface, such as the articular surface or the subchondral bone area. These instruments are also particularly suited to aid in the insertion of tools, devices, implants, etc. in a predetermined angular orientation with respect to the top surface of the bone to be treated (e.g., in a parallel or angled orientation). Accordingly, the present invention provides suitable instruments and associated methods for the surgical treatment of these bone defects, especially at the subchondral level near sclerotic bone.

Turning now to the drawings, FIG. 1 shows an exemplary embodiment of a navigation and positioning instrument 100 of the present disclosure, in relation to a bone 2. The navigation and positioning instrument 100 may be configured to provide simple, repeatable targeting of a local target area near a bone defect in a bone of a joint for percutaneous treatment of the defect. In addition, the navigation and positioning instrument 100 allows navigation and access to a target area from various angles, or locations, outside the bone 2. In the drawings and embodiments described, the bone may be a tibia 2 of a knee joint, for example. In the present example, the bone is a tibia 2 of a knee, with the tibial plateau 4, shaft 6 and tubercle 8 clearly identifiable from the drawing. For ease of illustration, the representative tibia 2 is shown clean and stripped of flesh and skin (i.e., the bone is shown without surrounding tissues). However, it is understood that the bone may be any other kind of joint bone.

The navigation and positioning instrument 100 of the present disclosure enables repeatable, controlled delivery of a device to a target area that sufficiently coincides at or near a bone defect in the subchondral level of the bone 2. In most cases, diagnosis and identification of a defect or defects that are consistent with the ones described for use with the present instruments and methods may be made by magnetic resonance imaging (MRI). However, it is also possible by simply palpating the patient (i.e., through manual examination) to identify an injury or defect suitable for treatment by the present instruments and methods.

As described and shown throughout the disclosure, the device in reference may be a pin. However, the term "device" as used herein is intended to refer generally to any number of implantable devices, tools or instruments suitable for bone treatment and/or repair. As will be described in more detail below, the device may be an implantable device, an insertion tool, a drill bit, an injection needle, a catheter, or any other surgical instrument. Accordingly, the navigation and positioning instrument 100 may be used to provide quick, easy, and repeatable targeting and access of an area at or near a bone defect by a number of instruments or implants that can perform any variety of treatment functions.

Figure 2A:
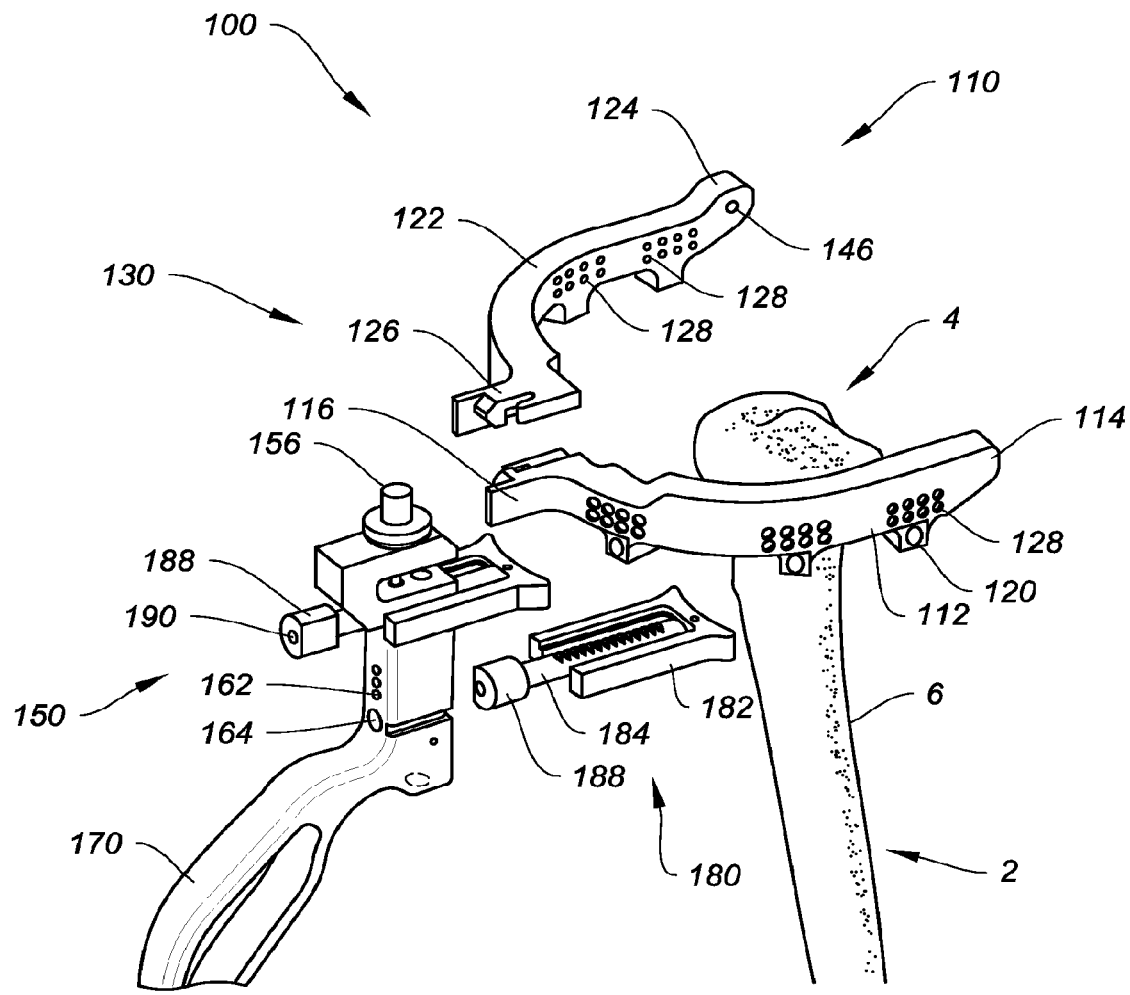
FIG. 2A is an exploded view of the instrument of FIG. 1.
Figure 2B:
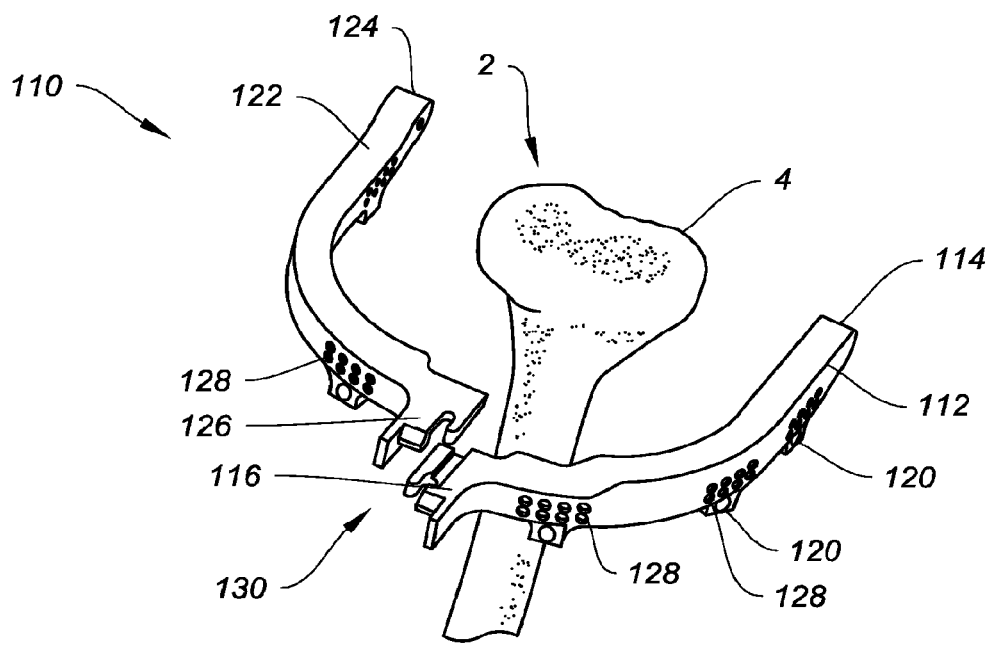
FIG. 2B is an exploded view of the guide frame of the instrument of FIG. 1.

The navigation and positioning instrument 100 may comprise two subcomponents: a guide frame 110, and a holder 150 for the guide frame 110. The guide frame 110 may comprise a rail that provides a framework and guide for positioning devices into the bone 2 to be treated. The guide frame 110 may be a single, unitary piece, or it may be formed of two or more connectable pieces. As shown in FIGS. 2A and 2B, the guide frame 110 may comprise a first rail arm 112 having a free end 114 and an attachment end 116, and a second rail arm 122 having a free end 124 and an attachment end 126. The attachment end 116 of the first arm 112 and the attachment end 126 of the second arm 122 may be configured to form a quick, easy detachable connection such as a dovetail connection 130, for example. Other types of connection mechanisms such as snap-fit arrangements may also be employed, of course, as is known in the art. (The connection of the guide frame components is such to guarantee or lock in the spatial relationship between the two components. The components are designed to be interlocked such that the relative movement or placement error between one component and the other is constrained and/or prevented.) Further, while each of the arms 112, 122 is shown to be circular, it is contemplated that the arms 112, 122 may be provided with any other geometric configuration such as an L-shape, U-shape, C-shape, etc. to create other shapes such as a square or rectangle, oval or polygon, when assembled together.

On each of the rail arms 112, 122 are device portals 128 configured in specific locations along their circumference. These device portals 128 act as positioning guides for inserting a device, such as a pin or other tool or implant, to the bone 2 to be treated. Accordingly, the guide frame 110 may serve as a jig, or a platform/frame to guide a device to a specific location on the bone 2 being treated. Each of the device portals 128 has a predetermined distance and spatial relationship relative to the other portals. The portals 128 serve as spatial reference or orientation or location markers for the clinician. Moreover, the device portals 128 are configured to provide accurate and controlled delivery of a device to the target site.

The device portals 128 may be configured at any desired angle relative to the guide frame 110. In one embodiment, the device portals 128 may be angularly configured to guide, or direct, the device in a parallel direction relative to the articular surface of the bone being treated. In other embodiments, the device portals 128 may be angularly configured in a parallel direction relative to the saggital, coronal, or transverse plane of the bone being treated. In still other embodiments, the device portals 128 may be angularly configured such that the trajectory of the device insertion (i.e., pin/implant approach) can be somewhat normal to the bone surface being penetrated, if desired. Thus, the navigation and positioning instrument 100 may be particularly suited to enable implants or other instruments to be inserted in a predetermined angular orientation to the top bone surface in an easy, fast and precise manner. In some instances, as will be shown and described later, pins 20 may be placed through the portals 128 provided on the guide frame 110 to secure the guide frame 110 to the bone 2. However, it is understood that the device portals 128 may also receive an insertion tool for the delivery of an implantable device or injectable material, if so desired.

Figure 2C:
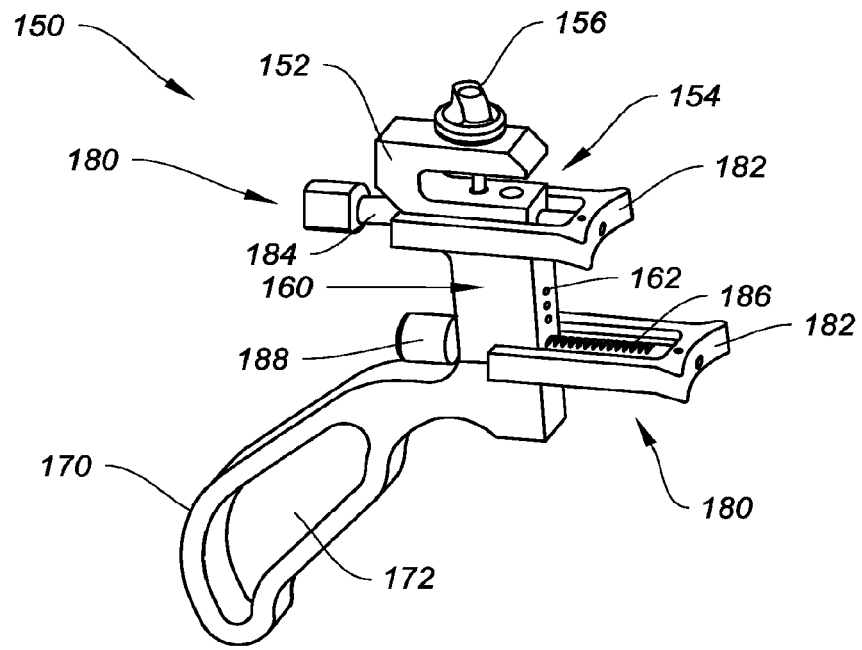
FIG. 2C is a perspective view of the guide frame holder of the instrument of FIG. 1.

A holder 150 may be provided for the guide frame. As shown in FIG. 2C, the holder 150 may include a head portion 152, a main body portion 160 and a handle portion 170. The head portion 152 may include an opening, such as a slot 154, for receiving the attachment ends 116, 126 of the first and second rail arms 112, 122. A locking mechanism, such as a catch and release or spring-loaded knob 156, may be provided so as to allow quick and easy attachment and detachment of the guide frame 110 from the holder 150. Along the length of the main body portion 160 are various portals. One or more device portals 162 may be provided for guiding a device, such as a pin or other tool, through the main body portion 160 and toward the bone 2 to be treated.

One or more stabilizer portals 164 may also be provided on the main body portion 160, as shown in FIG. 2A. The stabilizer portals 164 are configured to receive a stabilizer 180, and as illustrated may be configured to receive and hold two stabilizers 180. Each stabilizer 180 may comprise a bumper or plate 182 that is connected to a shaft 184. The shaft 184 may have teeth 186 on its surface for interfacing with corresponding surface features within the main body portion 160, thereby allowing ratcheting of the stabilizer 180 relative to the main body. The shaft 184 may include a knob 188 at its end to facilitate manual ratcheting of the stabilizer 180 in use. The knob 188 may further include a device portal 190, so that a pin or other tool may be inserted through the stabilizer 180 and toward the bone 2 to be treated, as needed. In use, the stabilizer 180 helps to brace the instrument 100 against the patient's body and further provides mechanical support for the holder 150.

At an opposite end from the head portion 152 the main body portion 160 extends into a handle 170. The handle 170 may be configured with a cutout portion 172 for gripping the instrument 100. Though not shown, device portals may also be provided on the handle portion 170 if so desired.

Figures 7A, 7B:
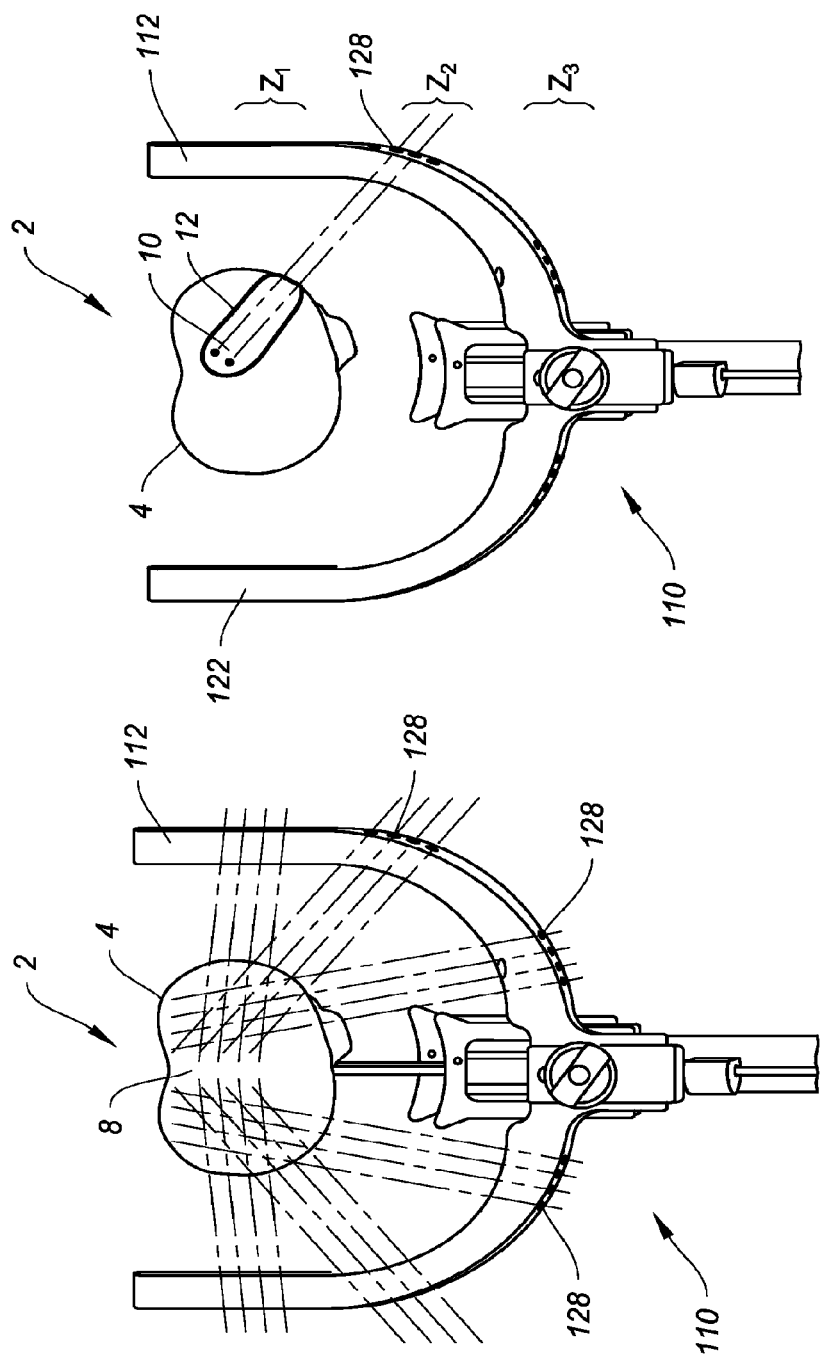
FIG. 7A illustrates various access points on the rail system of the instrument of FIG. 3.
FIG. 7B illustrates a step of navigating to an area near a bone defect using the instrument of FIG. 3.

As shown in FIGS. 7A and 7B, the navigation and positioning instrument 100 of the present disclosure provides several advantages, including simple, repeatable targeting of an area 12 near a defect 10 in a bone 2 for percutaneous treatment of that defect. The defect 10 could be, for example, a bone marrow lesion in the subchondral region of the bone 2 to be treated. The circular guide frame 110 serves as a 3-dimensional reference system to position devices towards the area 12 of the defect 10, while the various device portals 128 allow for percutaneous targeting of the area 12 near the defect 10. In addition, the instrument allows for repeatable targeting of the area 12 near the defect 10 in the range of about 5-10 mm below the articular surface or in the subchondral level of the bone 2.

Figure 3:
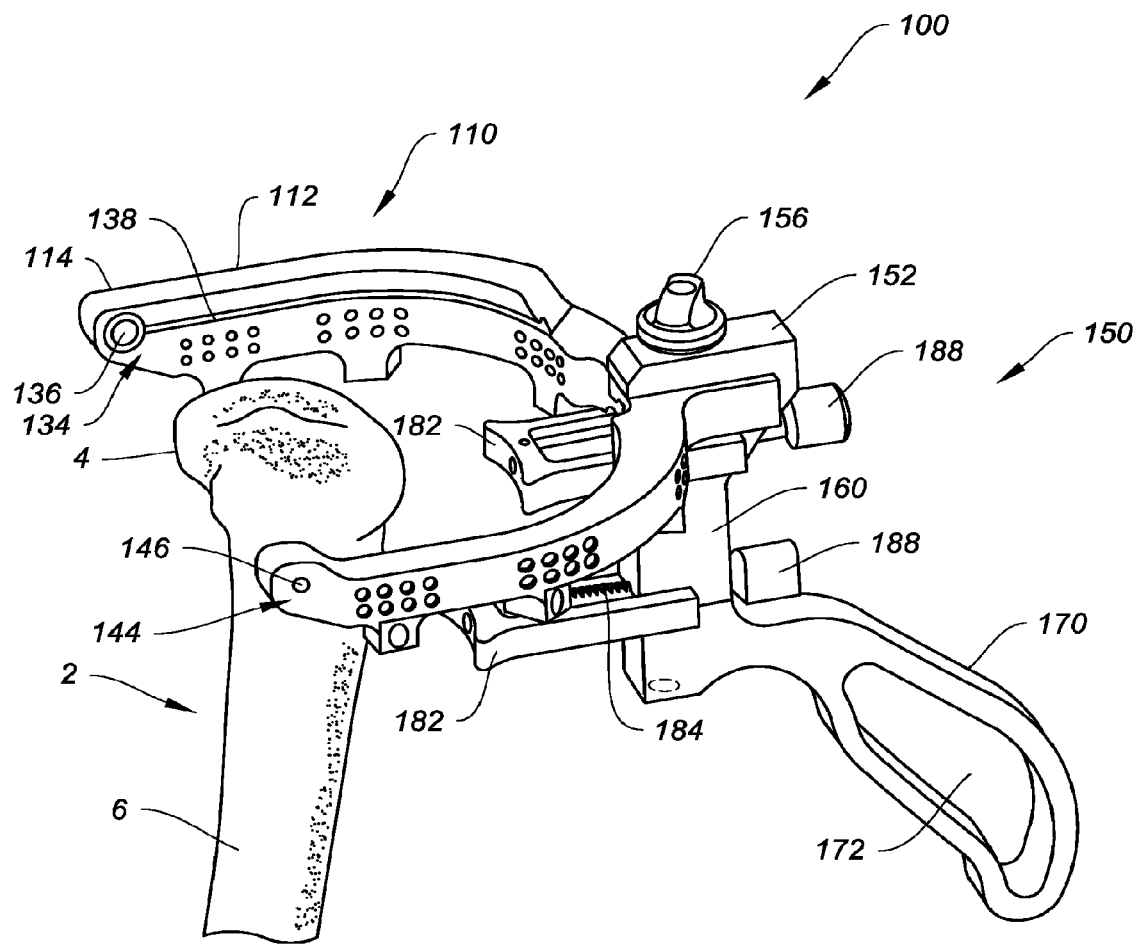
FIG. 3 is another perspective view of the instrument of FIG. 1 in use with a partial tibia.

The instrument 100 may be configured for use fluoroscopically to locate the area 12 near the defect 10 visually from above the cartilage surface. Each of the arms 112, 122 of the guide frame 110 are configured with visual markers 134, 144, respectively, that allow the user to align the instrument 100 to the bone 2 to be treated using anatomical landmarks. As shown in FIG. 3, first rail arm 112 includes a marker 134 comprising a circle 136 and a horizontal bar 138. Second rail arm 122 may include a marker 144 comprising a circle 146. The circle 146 may be slightly smaller than circle 136 of the first rail arm 112. Each of the markers 134, 144 may be radiopaque, though it is contemplated that other types of visual markers may also be employed. Furthermore, the markers may have any other type of geometric shape or configuration, such as a square, oval, star, teardrop, etc. The markers 134, 144 facilitate proper alignment of the instrument 100 relative to the bone 2 to be treated.

The navigation and positioning instrument 100 of the present disclosure is suitable for use where it is desirable to treat a local area 12 specific to a defect 10 of a bone 2 using a percutaneous approach. The instrument 100 may be used with a C-arm in conjunction with an MRI template system for identifying the area 12 to be treated, and for aligning or positioning devices intended to be introduced to that area 12. The instrument 100 is aligned to the bone 2 by reference to the bone's own natural geometry and takes into account anterior-posterior (AP) as well as vertical placement. Through fixation of vertical and anterior-posterior placement to an anatomical reference, the targeting portal grid of the guide frame correlates to a template mapping grid used with the MRI.

Figure 4:
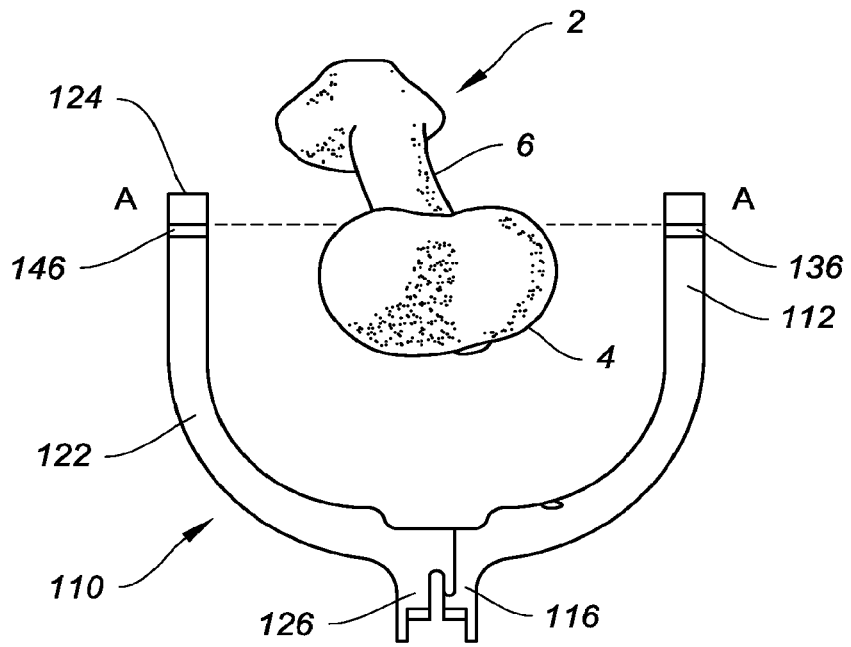
FIG. 4 illustrates a step of orienting the instrument of FIG. 3 in view of the partial tibia.
Figure 5:
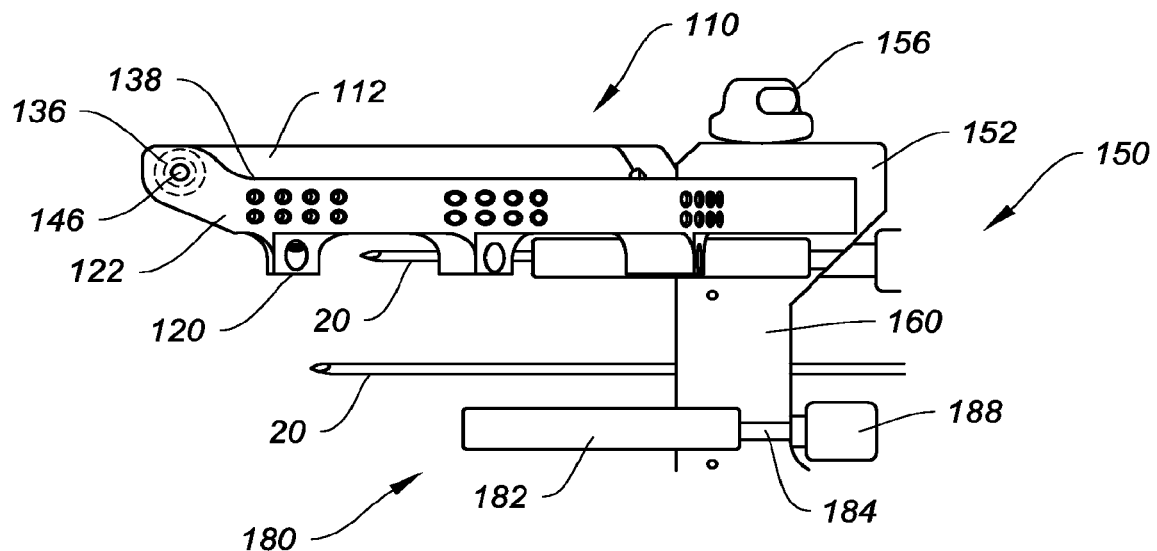
FIG. 5 is a side view of the instrument of FIG. 3.
Figure 6A:
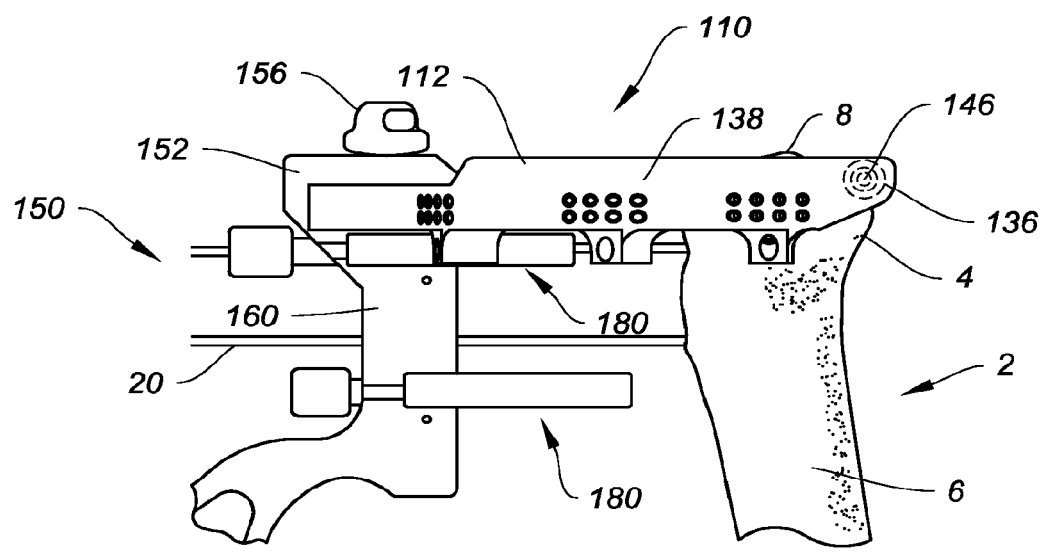
FIG. 6A is a side view of the instrument of FIG. 3 aligned with the partial tibia.
Figure 6B:
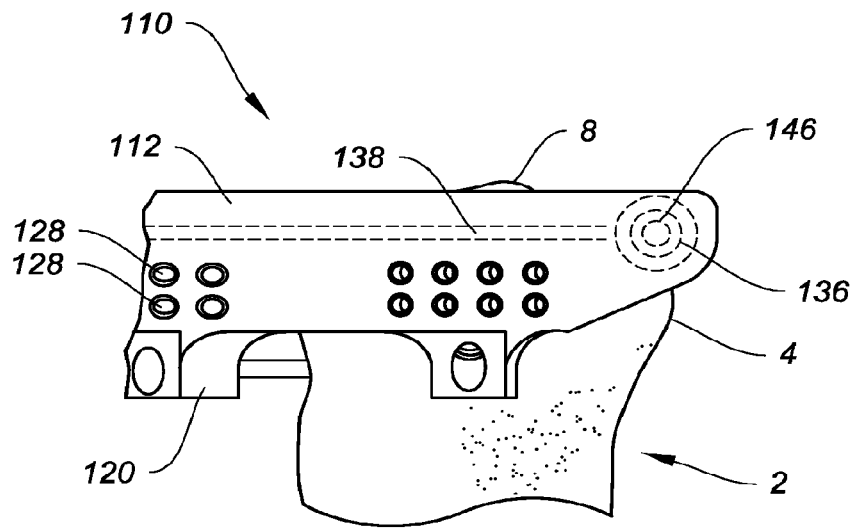
FIG. 6B is yet another side view of the instrument of FIG. 3 aligned with the partial tibia.

In one exemplary method of use, the navigation and positioning instrument 100 is firstly placed in the correct location to the bone 2. Placement can be achieved using fluoroscopic visualization in view of the anatomic landmarks on the bone 2 being treated. In the present example, the bone 2 to be treated is a tibia, and the C-arm would be lined up perpendicular to the sagittal plane in line with the tibial plateau 4. Next, the guide frame 110 would be positioned in reference to the tibial plateau 4. The radiopaque markers 134, 144 on each of the rail arms 112, 122 are aligned such that the smaller circle 146 lines up with the larger circle 136, as shown in FIG. 5. The circles 136, 146 are aligned to the back of the tibial plateau 4, as shown by lines A-A in FIG. 4. As further shown in FIG. 6A, the circles 136, 146 match up to the back corner of the tibial plateau 4 in the anterior-posterior view, and the horizontal bar 138 of marker 134 lines up with the tibial plateau 4 in the vertical view, as shown in FIG. 6B. The instrument 100 could be centered to the tubercle 8. As previously discussed, the markers 134, 144 could comprise any kind of shape other than circles and lines, and could be configured to reference other anatomical landmarks.

Turning back to FIGS. 7A and 7B, the instrument 100 and specifically the rail arms 112, 122 of the guide frame 110 are configured with a plurality of device portals 128. As shown, each rail arm 112, 122 may include three sets of portals 128 at zones $Z_1$, $Z_2$ and $Z_3$. One or more portals 128 may be contained within each zone, and preferably two or more portals 128 may be provided. In one embodiment, four portals 128 are provided at each distinct zone. Each portal 128 may have a different trajectory. The angles of the device portals 128 are chosen to provide for maximum coverage of the tibia given the three zones of parallel matrices of portals 128. This ensures that any inserted device or implant is placed parallel to the articulating or loaded surface so as to act as a supporting member or beam under the loaded/articulating surface of the joint. This also ensures that, for any matrix or group of portals 128, the portals 128 in that matrix are parallel so that if multiple implants or pins are inserted they do no intersect or collide into each other. Accordingly, the number of zones and number of portals 128 in each zone should be sufficient to cover all relevant points on the tibial plateau 4, as seen in FIG. 7A. In this manner, a defect 10 could be located in a particular region 12 and treated through the corresponding device portal(s) 128 once the trajectory for entry has been selected, as shown in FIG. 7B.

After the instrument 100 is properly aligned and centered with respect to the anatomical landmarks of the tibia 2, the instrument 100 may be secured in place. If so desired, the stabilizers 180 may be employed and positioned against the patient's leg. These stabilizers 180 help to support the instrument 100 relative to the tibia 2. The stabilizers 180 may be configured to ratchet relative to the holder 150 in order to allow adjustability of the stabilizers 180 to the tibia 2. If desired, the instrument 100 may be configured so that the instrument 100 rests on the fat or skin of the patient's leg. In addition, the head portion 152 of the holder 150 may be configured to allow adjustability of the anterior-posterior depth of the guide frame 110 within the slotted opening 154.

Figure 8:
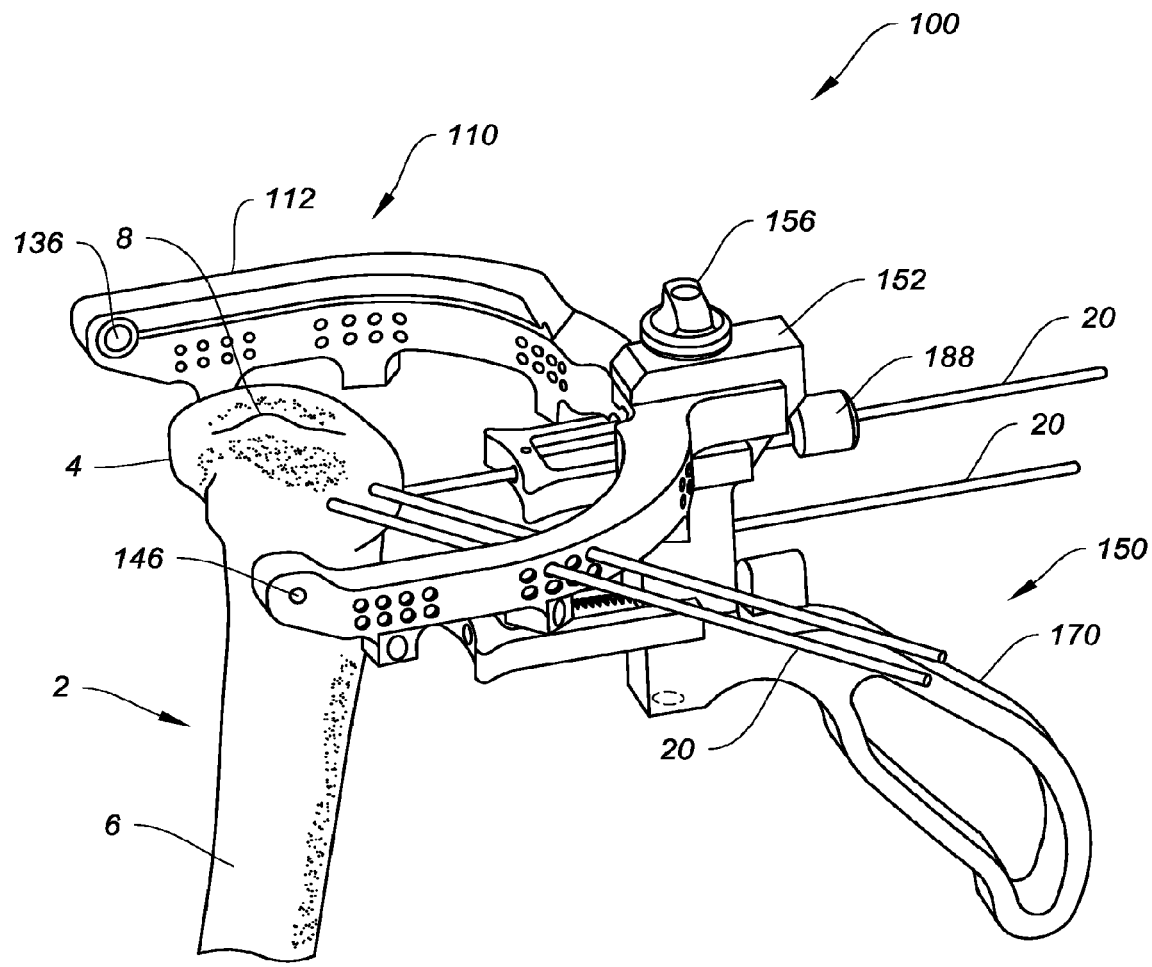
FIG. 8 represents a method of positioning a device in an area near a bone defect using the instrument of FIG. 3.

As shown in FIG. 8, one or more devices or pins 20 may be used to secure the instrument to the tibia 2. The pins 20 may be placed percutaneously through the device portals 128 of the guide frame 110, or through the holder 150 such as through the knob 188 of the stabilizers 180 or through the main body portion 160, as shown in greater detail in FIG. 9.

In the examples shown, the device may be a pin 20. However, the term "device" is used herein to refer generally to any number of implantable devices, materials and instruments suitable for bone treatment and/or repair. For example, the device may be an implantable device, an insertion tool, a drill bit, an injection needle, a catheter, or any other surgical instrument. The device may be marked with indicia or colored bands representing depth so that the clinician is better able to control the depth into the bone.

Figure 11:
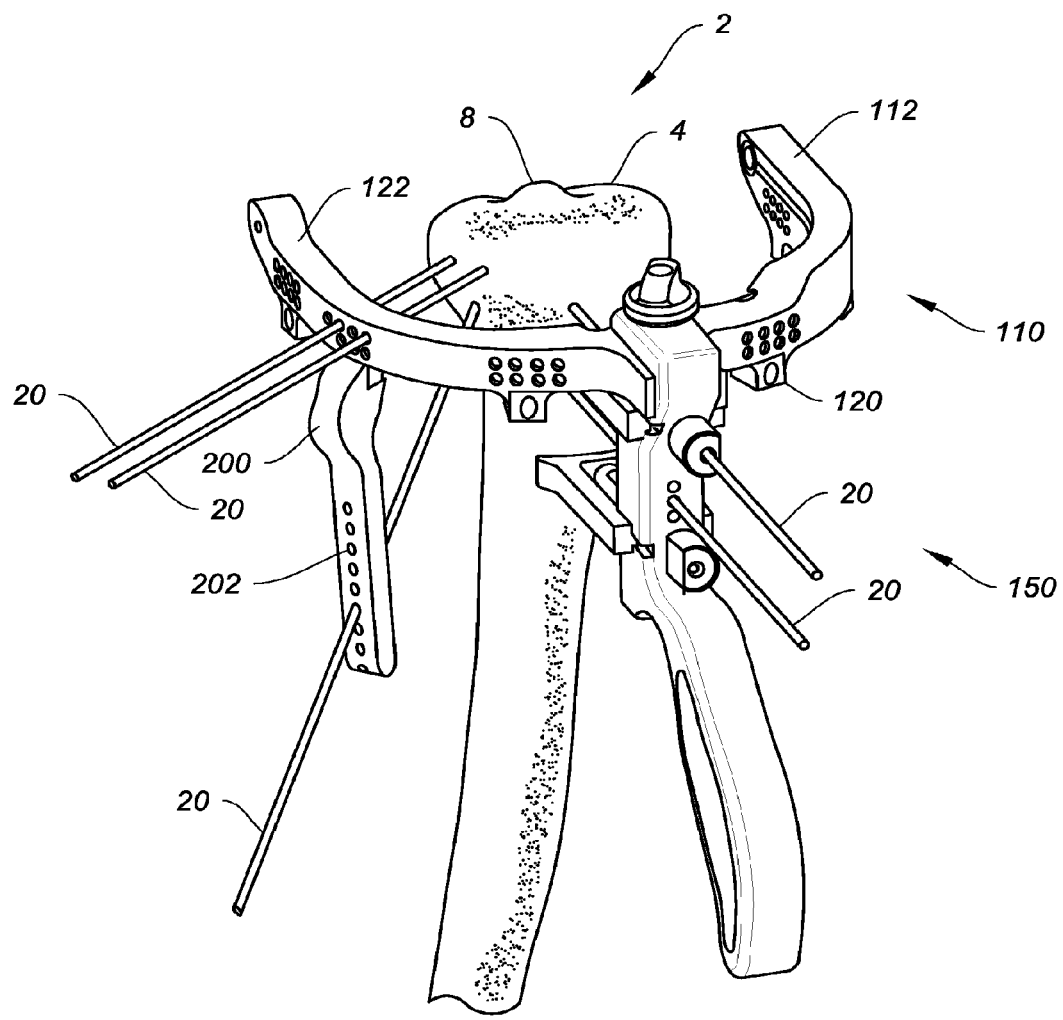
FIG. 11 is a perspective view of another embodiment of the instrument of the present invention with the distal guide of FIG. 10.

Additional stabilization components or positioning guides may also be employed. For example, as shown in FIG. 10, an optional inferior guide 200 may also be provided with navigation and positioning instrument 100 of the present disclosure. The detachable inferior guide 200 may include one or more device portals 202 for receiving a device. The device may be, for example, a pin, needle or drill bit. In one instance, the device may be a drill to drill a hole in the bone 2, for example. In another instance, the device may be a device insertion tool for introduction of an implantable device, for example. Accordingly, as illustrated in FIG. 11, the inferior guide 200 offers a distal, or inferior approach guide, for targeting the lower area of the target site 12 or other tissue area from different angular approaches through device portals 202. The inferior guide 200 may be provided with a knob 204 that can be quickly attached to any one of a plurality of tabs 120 along the bottom edge of the guide frame 110. However, it is contemplated that any known mechanism for attaching the inferior guide 200 to the guide frame 110 may be provided, so long as the mechanism allows quick and easy detachment, without disturbing any other components of the instrument 100 or tools that may have been employed during its use.

Figure 12A:
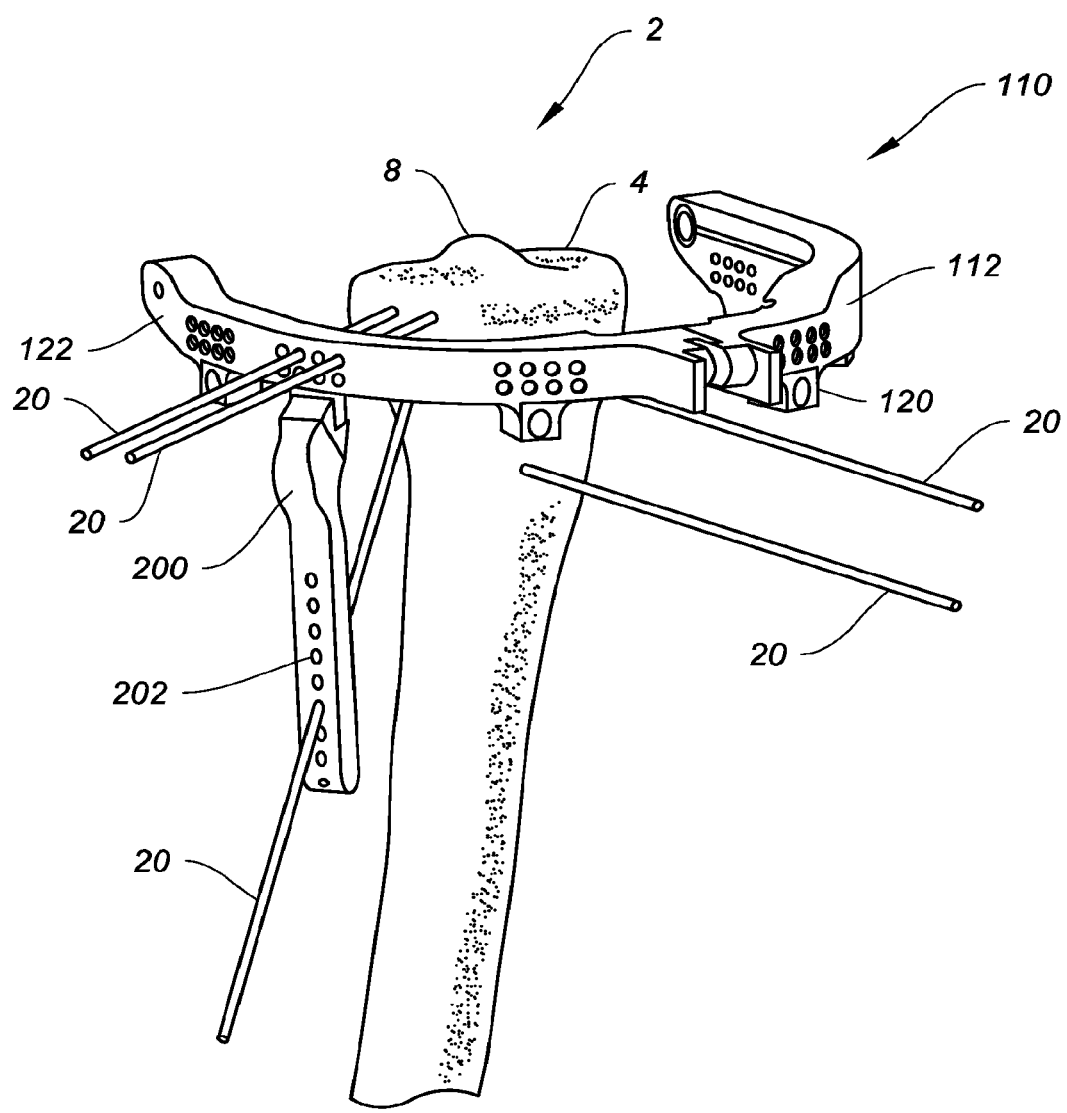
FIGS. 12A-12C show steps of using the instrument of FIG. 11 to position devices into the area near a bone defect.
Figure 12B:
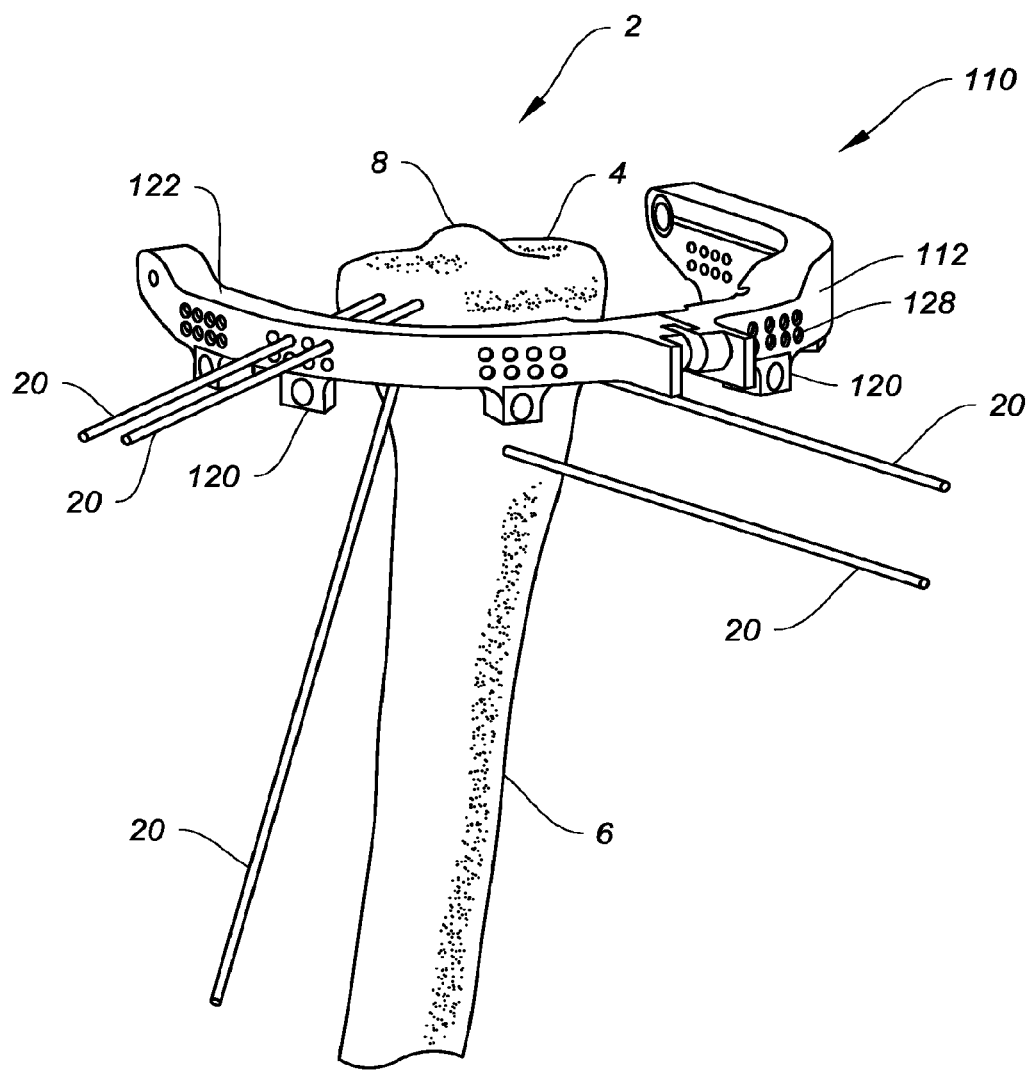
Figure 12C:
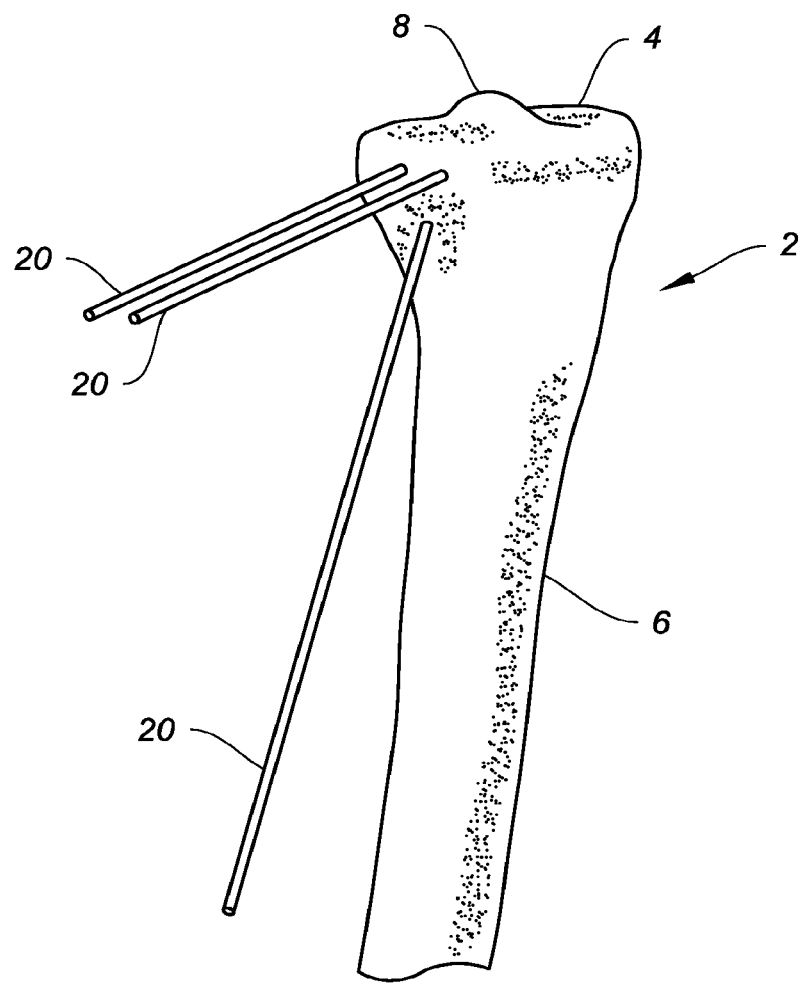

After placement of the pins 20 to the tibia 2, it is possible to disassemble the instrument 100 piecemeal. The instrument 100 of the present disclosure is configured with multiple quick release mechanisms for removing one or more portions of the instrument 100 during use. For example, as shown in FIGS. 12A-12C, the holder 150 may be detached from the guide frame 110 (see FIG. 12A.) In addition, the inferior guide 200 may be detached from the guide frame, as shown in FIG. 12B. Finally, the guide frame 110 may be removed, leaving only the pins 20 to mark the location of the area 12 near the defect 10 to be treated (see FIG. 12C.) By removing one or more portions of the instrument 100, the user may be able to open up a larger work space for the surgery, as desired.

Figure 13B:
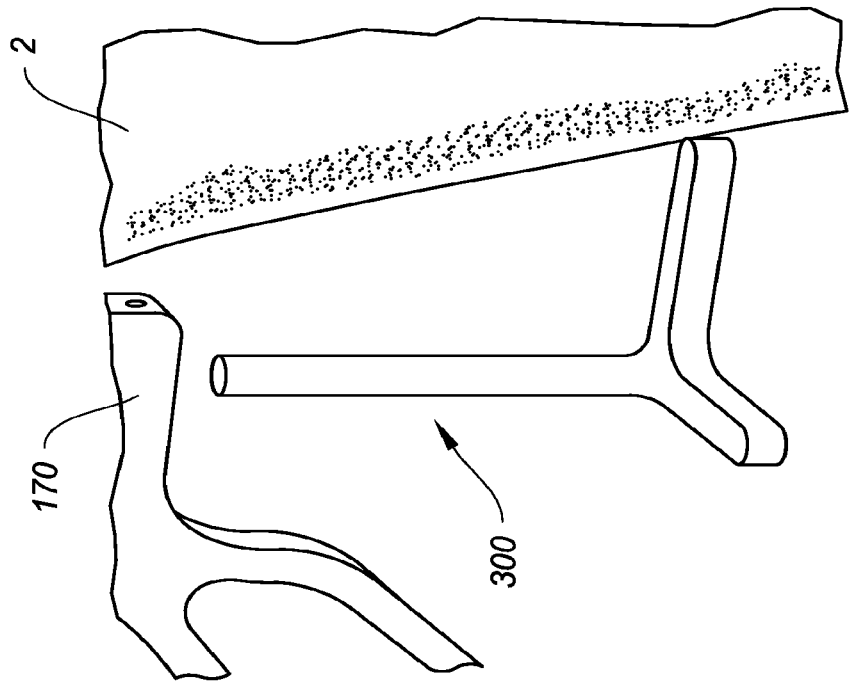
FIG. 13B shows the leg brace and instrument of FIG. 13A unattached.
Figure 13A:
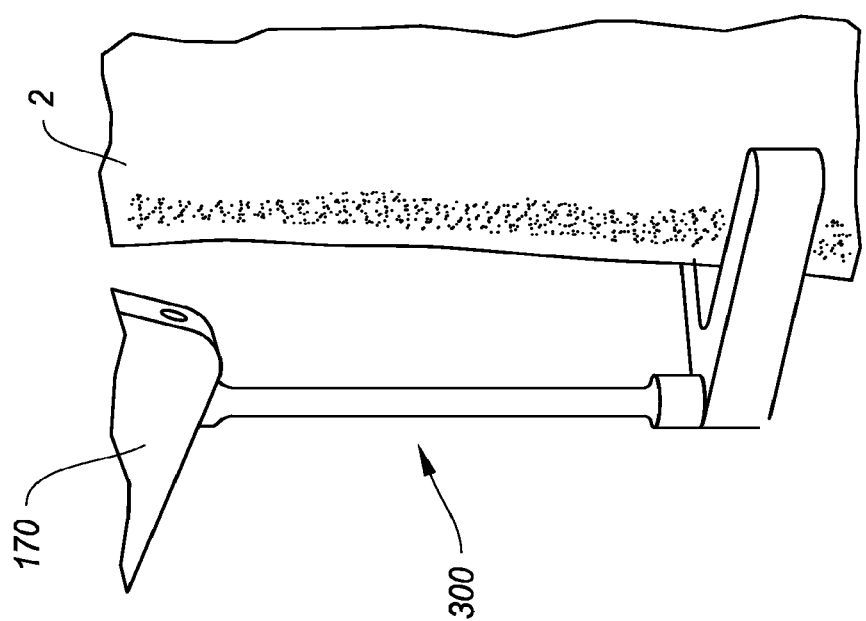
FIG. 13A shows another exemplary embodiment of the instrument of the present invention with an optional leg brace.

FIGS. 13A and 13B show yet another optional stabilization component that can be used with the navigation and positioning instrument 100 of the present disclosure. As shown, a leg brace 300 may be provided for further stabilization of the instrument 100 to the patient's leg. The brace 300 may be of the Y-shaped kind and be configured for quick and easy detachment to the handle portion 170 of the holder 150.

A number of treatment modalities, and associated devices, instruments and related methods of use can be employed using the navigation and positioning instrument 100 just described. In one treatment modality, the target area 12 local to the defect 10 can be strengthened by introduction of a hardening material at the site. For example, polymethylmethacrylate (PMMA) or calcium phosphate (CaP) cement injections can be made at the defect site. PMMA injection may increase the mechanical strength of the bone, allowing it to withstand greater mechanical stresses. CaP cement injection may also increase the mechanical strength of the bone, while also stimulating the localized region for bone fracture repair. In one embodiment, the injection can be made parallel to the joint surface. In another embodiment, the injection can be made at an angle to the joint surface. In yet another embodiment, the injection can be made below the target area 12. In another embodiment, there could be provided the combination of an implant or device inserted parallel to the joint surface and cement injection can be made at an angle below the target area.

In another treatment modality, the target area 12 can be stimulated to improve the body's natural healing process. For example, in one embodiment of this treatment modality, small holes may be drilled at the region of the defect to increase stimulation (e.g., blood flow, cellular turnover, etc.) and initial bone repair. However, it is understood that holes may be created using any number of cavity creation tools, other than drill bits, such as with a tamp, series of cannulas, or other known tools. In another embodiment, after holes are drilled an osteogenic, osteoinductive, or osteoconductive agent may be introduced to the site. Bone graft material, for example, may be used to fill the hole. This treatment modality may create a better load supporting environment leading to long term healing.

In yet another treatment modality, an implantable device may be implanted into target area 12 to provide mechanical support to the damaged or affected bone region, such as where an insufficiency fracture has occurred. The implant may help create a better load distribution in the subchondral region. In the knees, the implant may support tibio-femoral compressive loads. In addition, the implant may mechanically integrate sclerotic bone with the surrounding healthy bone tissue. Exemplary implantable devices are disclosed in co-pending and co-owned U.S. patent application Ser. No. 12/950,306, filed Nov. 19, 2010 and entitled "IMPLANTABLE DEVICES FOR SUBCHONDRAL TREATMENT OF JOINT PAIN," U.S. patent application Ser. No. 12/950,273, filed Nov. 19, 2010 and entitled "IMPLANTABLE DEVICES FOR SUBCHONDRAL TREATMENT OF JOINT PAIN," and U.S. patent application Ser. No. 12/950,183, filed Nov. 19, 2010 and entitled "BONE-DERIVED IMPLANTABLE DEVICES FOR SUBCHONDRAL TREATMENT OF JOINT PAIN," the contents of which are herein incorporated in their entirety by reference.

The process of compacting bone tissue at the target site may be a treatment modality by itself. Since the navigation and positioning instrument 100 of the present disclosure provides the advantage of controlled and repeatable access to an area 12 near a defect 10 from a variety of angles or trajectories, the navigation and positioning instrument 100 may be used to compact bone tissue at the target area 12 from multiple approaches, or angles, creating a starburst-like pattern.

The instrument 100 of the present disclosure is intended to work with image mapping or template systems. The device portals 128 should be configured with trajectories that can correlate to the template system. In this manner, the insertion of the device through the instrument 100 and to the defect area 12 can correlate with the mapped image of the defect. Such mapping may be done by way of, for example, MRI images that can be either pre-operative or intra-operative, for instance.

While each of the above-mentioned treatment modalities may be administered independent of one another, it is contemplated that any combination of these modalities may be applied together and in any order so desired, depending on the severity or stage of development of the bone defect(s).

Other embodiments of the invention will be apparent to those skilled in the art from consideration of the specification and practice of the disclosure provided herein. It is intended that the specification and examples be considered as exemplary only, with a true scope and spirit of the disclosure being indicated by the following claims.

What is claimed is:

1. A guidance instrument for controlled delivery of a device to a target area of a bone, comprising:
    a guide frame having at least one rail arm and a plurality of device portals on the arm arranged in a grid pattern and configured for locating the target area, each portal defining an angular trajectory and being configured to provide controlled delivery of the device to the target area, the guide frame further including at least one visual marker that enables the guide frame to be aligned relative to an anatomical landmark on the bone to be treated by visualization of the marker; and
    a stabilizer element including an engagement portion configured to contact the bone or surrounding tissue.

2. The guidance instrument of claim 1, wherein the stabilizer element is removably coupled to the guide frame.

3. The guidance instrument of claim 1, wherein the stabilizer element is adjustable relative to the guide frame.

4. The guidance instrument of claim 1, wherein the stabilizer element is configured to contact bone or surrounding tissue in more than one location.

5. The guidance instrument of claim 1, wherein the at least one rail arm is shaped so as to define a portion of a circle.

6. The guidance instrument of claim 1, wherein the at least one visual marker includes a first visual marker configured for alignment with a superior surface of a tibial plateau.

7. The guidance instrument of claim 6, wherein the at least one visual marker includes a second visual marker configured for alignment with a posterior portion of the tibial plateau.

8. The guidance instrument of claim 1, wherein the at least one visual marker is radiopaque.

9. The guidance instrument of claim 1, wherein the at least one visual marker is configured to be visualized through fluoroscopy.

10. The guidance instrument of claim 1, wherein the at least one rail arm comprises a pair of rail arms, each arm having a plurality of device portals.

11. A guidance instrument or controlled delivery of a device to a target area of a bone, comprising:
    a guide frame having at least one rail arm and a plurality of device portals arranged in two or more zones relative to the guide frame and configured for locating the target area, each portal defining an angular trajectory and being configured to provide controlled delivery of the device to the target area, the angular trajectories of the device portals arranged to form a targeting portal grid; and
    a stabilizer element including an engagement portion configured to stabilize the guide frame and register a position of the guide frame relative to the target area of the bone.

12. The guidance instrument of claim 11, further comprising at least one visual marker that enables the guide frame to be aligned relative to an anatomical landmark on the bone by visualization of the marker.

13. The guidance instrument of claim 11, wherein the stabilizer element is removably coupled to the guide frame.

14. The guidance instrument of claim 11, wherein the device is an insertion tool, drill, cavity creation tool, injection needle, or catheter.

15. The guidance instrument of claim 11, wherein the device is an implantable device.

16. The guidance instrument of claim 11, further comprising an auxiliary guide having one or more portals, the auxiliary guide configured for releasable attachment to the guide frame.

17. A guidance instrument for controlled delivery of a device to a target area of a bone, comprising:
    a guide frame having a first guide portion and a second guide portion, the first and second guide portions each including at least one device portal defining an angular trajectory and a visual marker, wherein the angular trajectories of the device portals are arranged to form a targeting portal grid, and wherein the guide frame can be aligned relative to an anatomical landmark on the bone by aligning the visual marker of the first guide portion with the visual marker of the second guide portion; and
    a stabilizer element including an engagement portion configured to be positioned against the bone or surrounding tissue.

18. The guidance instrument of claim 17, wherein the stabilizer element is removably coupled to the guide frame.

19. The guidance instrument of claim 17, wherein the visual markers are radiopaque.

* * * * *